(12) United States Patent
Hendricks et al.

(10) Patent No.: US 9,719,878 B2
(45) Date of Patent: Aug. 1, 2017

(54) PHOTONIC ARTICLE, PROCESS FOR MAKING AND USING SAME

(71) Applicant: NATIONAL INSTITUTE OF STANDARDS AND TECHNOLOGY, Gaithersburg, MD (US)

(72) Inventors: Jay H. Hendricks, Clarksburg, MD (US); Gregory F. Strouse, Frederick, MD (US); Jacob E. Ricker, Gaithersburg, MD (US); Douglas A. Olson, North Potomac, MD (US); Gregory E. Scace, Laytonsville, MD (US); Jack A. Stone, Silver Spring, MD (US); Patrick F. Egan, Rockville, MD (US)

(73) Assignee: THE UNITED STATES OF AMERICA, AS REPRESENTED BY THE SECRETARY OF COMMERCE, Washington, DC (US)

(*) Notice: Subject to any disclaimer, the term of this patent is extended or adjusted under 35 U.S.C. 154(b) by 115 days.

(21) Appl. No.: 14/664,247

(22) Filed: Mar. 20, 2015

(65) Prior Publication Data
US 2016/0018280 A1  Jan. 21, 2016

Related U.S. Application Data

(60) Provisional application No. 62/104,106, filed on Jan. 16, 2015.

(51) Int. Cl.
| | |
|---|---|
| *G01L 11/02* | (2006.01) |
| *G01K 11/00* | (2006.01) |
| *G01N 21/45* | (2006.01) |

(52) U.S. Cl.
CPC ............ *G01L 11/02* (2013.01); *G01K 11/00* (2013.01); *G01N 21/45* (2013.01)

(58) Field of Classification Search
None
See application file for complete search history.

(56) References Cited

U.S. PATENT DOCUMENTS

| | | | | |
|---|---|---|---|---|
| 6,539,136 | B1* | 3/2003 | Dianov | G01L 9/0079 250/227.11 |
| 2005/0215031 | A1* | 9/2005 | Ouchi | G01J 3/0256 438/459 |

OTHER PUBLICATIONS

Jay H. Hendricks, Measuring Pressure and Vacuum with Light, NIST, Sensor Science Division Seminar, Oct. 7, 2014, pp. 1-39.
Jay H. Hendricks, World First Photonic Pressure Sensor Outshines Traditional Mercury Standard, Physical, Measurement Laboratory (PML), Oct. 29, 2014, www.nist.gov/pml/div685/grp01/102814-resurresensor.cfm.

* cited by examiner

*Primary Examiner* — Andre Allen
(74) *Attorney, Agent, or Firm* — Toby D. Hain

(57) ABSTRACT

An article to determine a sample condition includes a substrate; a reference optical cavity disposed on the substrate and comprising a reference cavity, the reference optical cavity being configured to support a reference optical resonance and to maintain an axial length of the reference cavity; and a sample optical cavity disposed on the substrate and comprising a sample cavity, the sample optical cavity being configured to support a sample optical resonance and to maintain an axial length of the sample cavity.

18 Claims, 32 Drawing Sheets

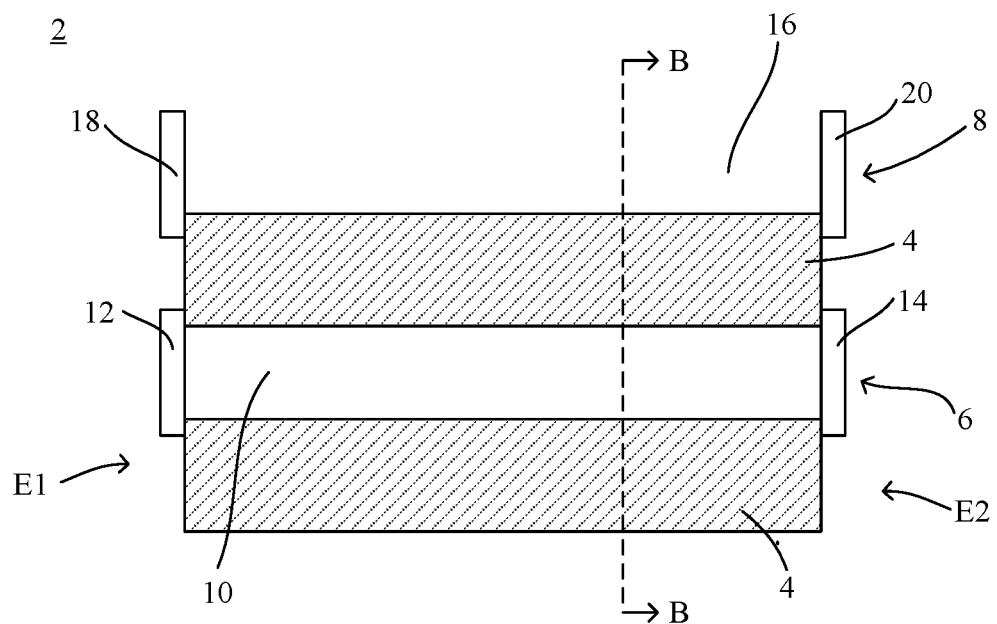
FIG. 2A
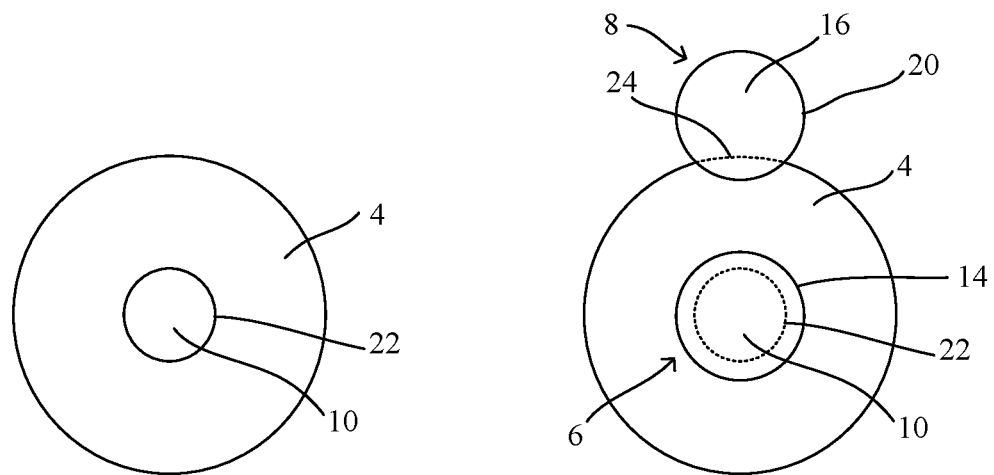
FIG. 2B
FIG. 2C

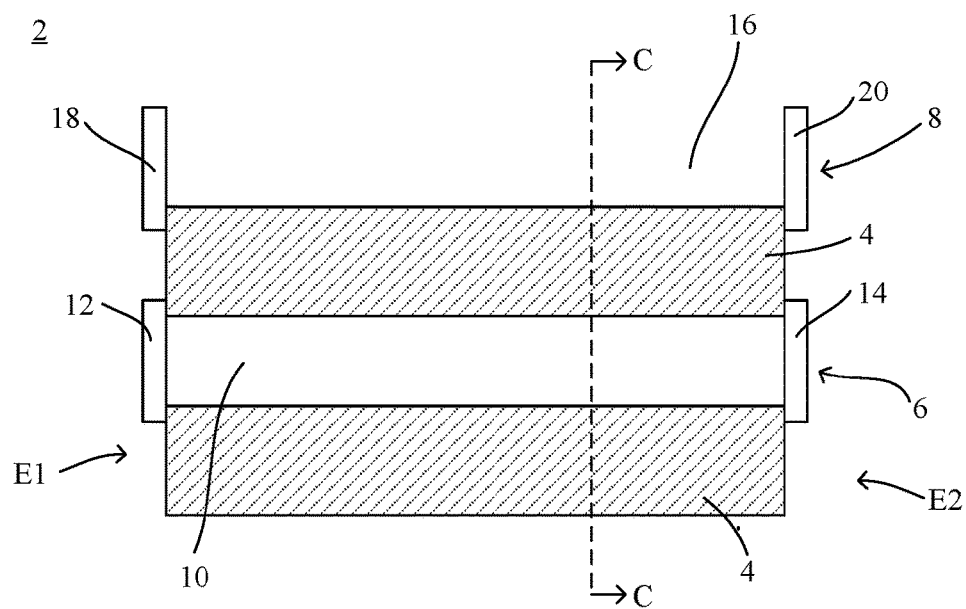
FIG. 3A
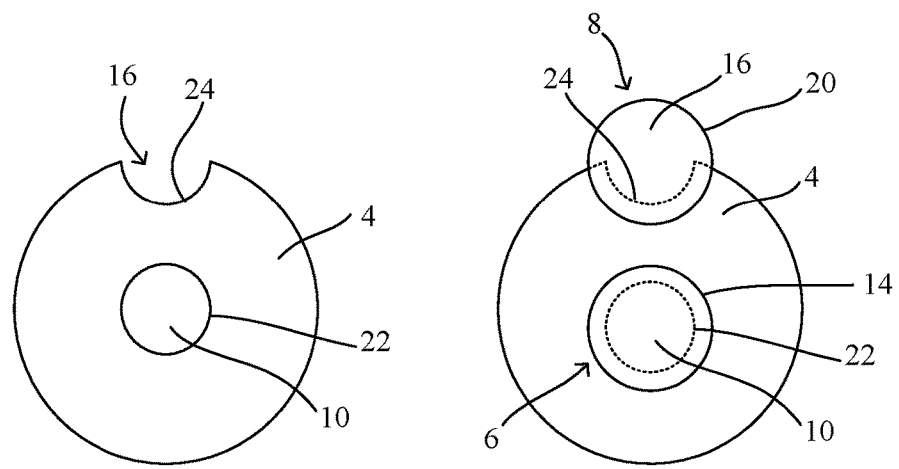
FIG. 3B
FIG. 3C

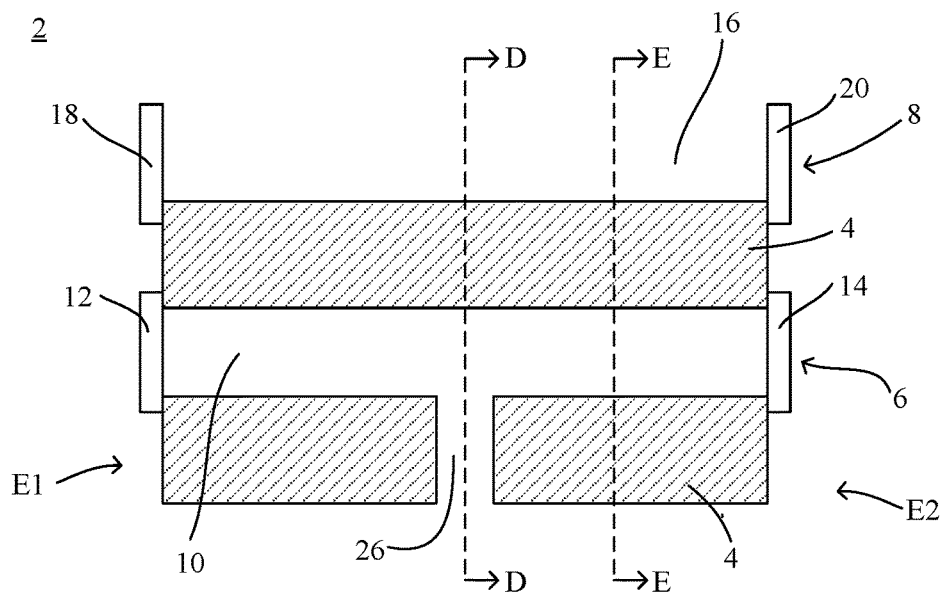
FIG. 4A
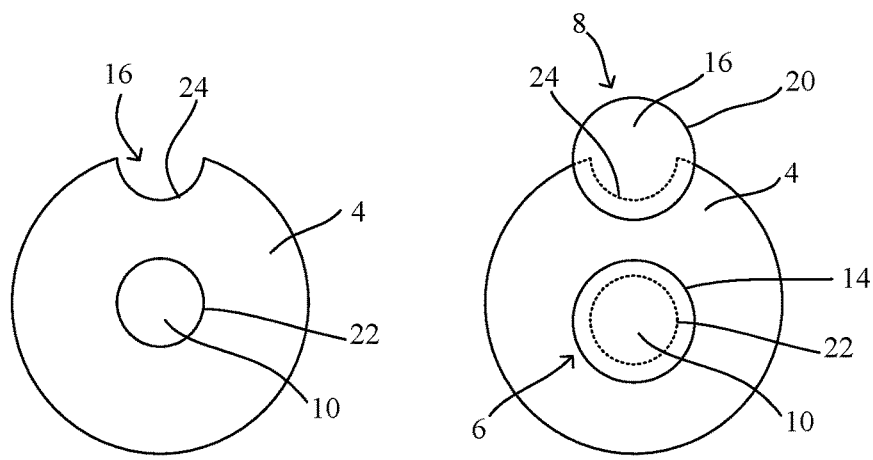
FIG. 4B
FIG. 4C
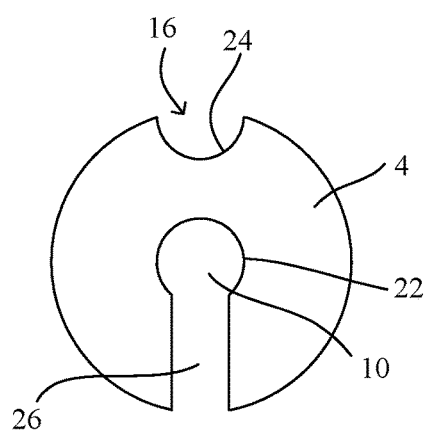
FIG. 4D

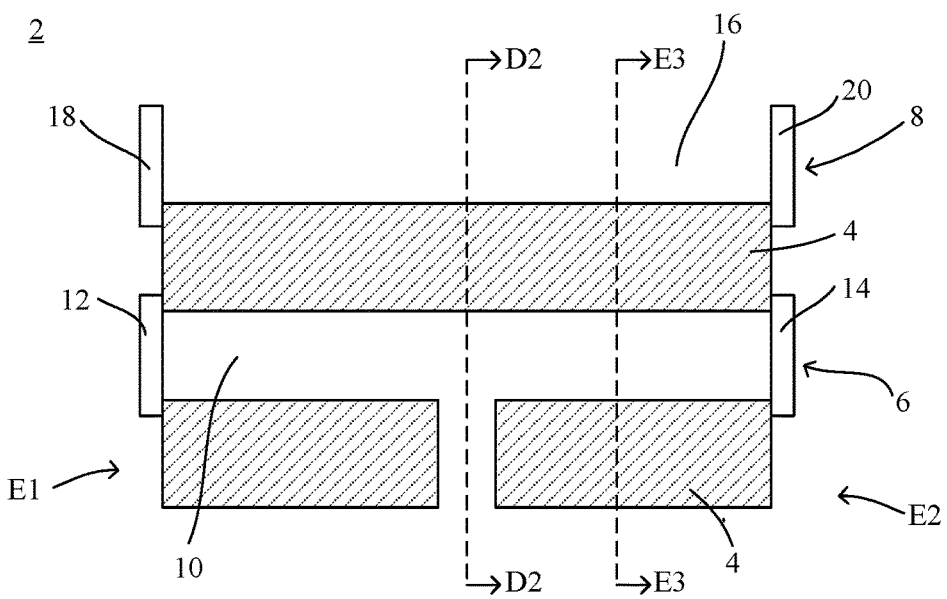
FIG. 5A
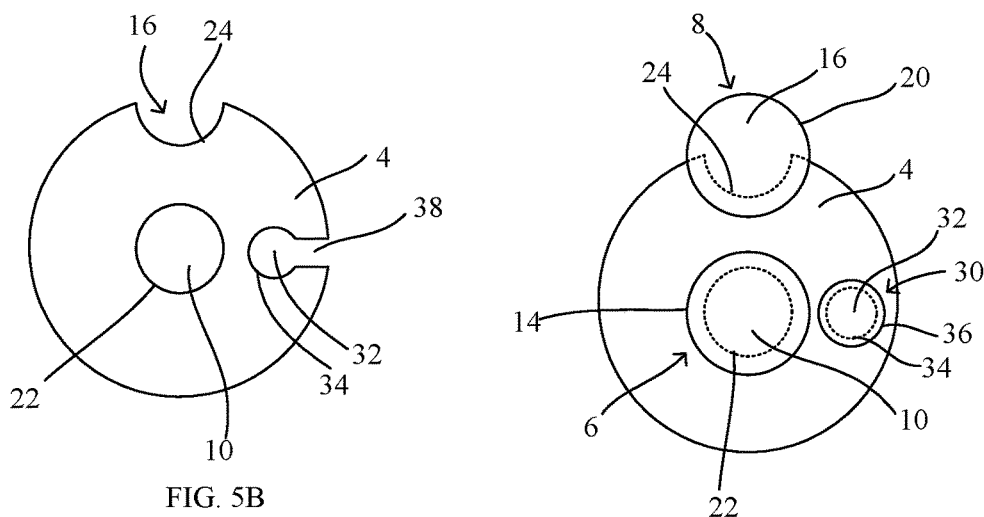
FIG. 5B
FIG. 5C
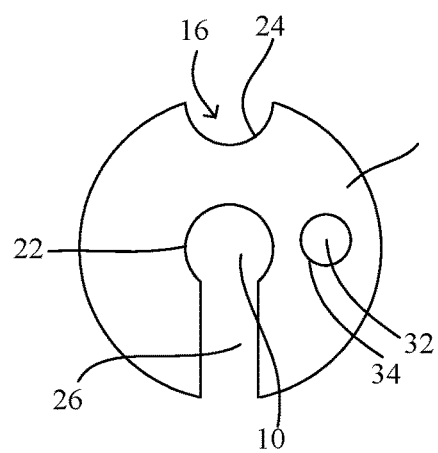
FIG. 5D

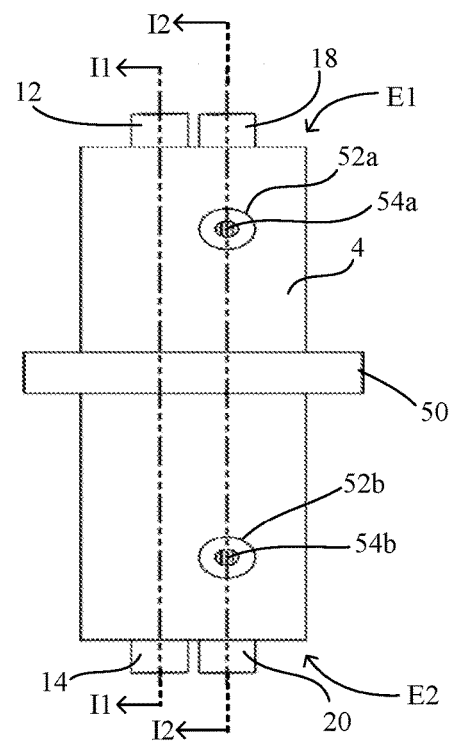
FIG. 8F
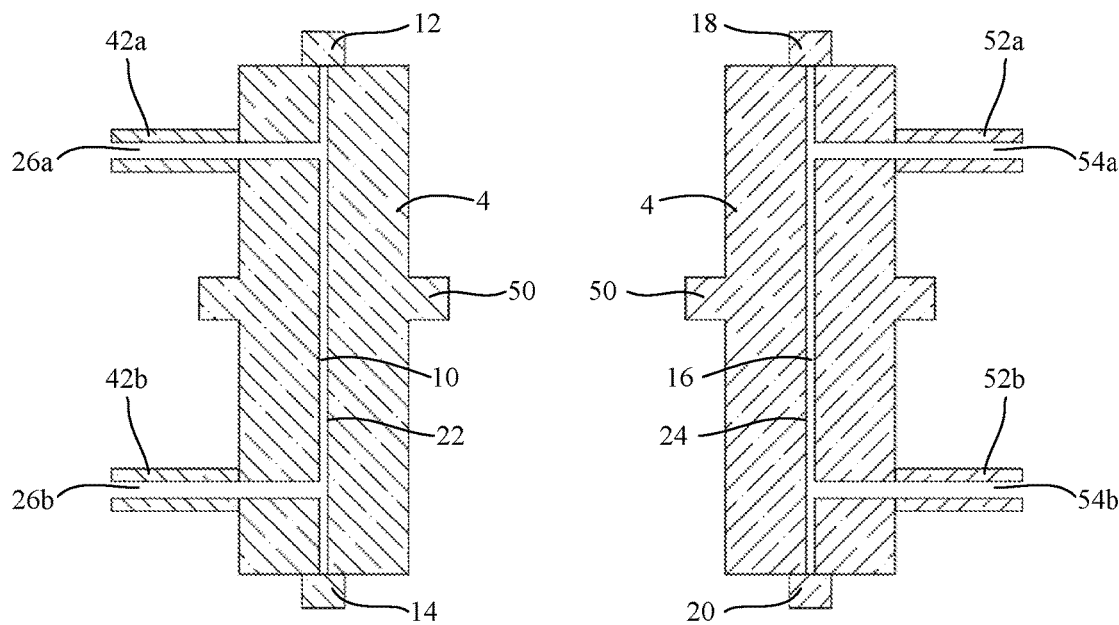
FIG. 8G
FIG. 8H

PHOTONIC ARTICLE, PROCESS FOR MAKING AND USING SAME

CROSS REFERENCE TO RELATED APPLICATIONS

The present application claims the benefit of U.S. Provisional Patent Application Ser. No. 62/104,106 filed Jan. 16, 2015, the disclosure of which is incorporated herein by reference in its entirety.

STATEMENT REGARDING FEDERALLY SPONSORED RESEARCH

This invention was made with United States government support from the National Institute of Standards and Technology. The government has certain rights in the invention.

STATEMENT OF GOVERNMENT INTEREST

This invention may be manufactured or used by or for the government of the United States of America without the payment of any royalties thereon or therefore.

BRIEF DESCRIPTION

The above and other deficiencies are overcome by, in an embodiment, an article comprising: a substrate; a reference optical cavity disposed on the substrate and comprising a reference cavity, the reference optical cavity being configured to support a reference optical resonance and to maintain an axial length of the reference cavity; and a sample optical cavity disposed on the substrate and comprising a sample cavity, the sample optical cavity being configured to support a sample optical resonance and to maintain an axial length of the sample cavity.

Further disclosed is an article comprising: a first substrate; a second substrate spaced apart from the first substrate and opposingly disposed to the first substrate; a plurality of first mirrors disposed on the first substrate; a plurality of second mirrors disposed on the second substrate; a variable length member interposed between the first substrate and the second substrate and comprising an internal hollow portion; a reference optical cavity configured to support a reference optical resonance and comprising: a reference cavity; and a first pair of mirrors comprising: one of the first mirrors; and one of the second mirrors, such that the first pair of mirrors is opposingly arranged to one another, and the reference cavity is interposed between the first pair of mirrors and comprises the internal hollow portion; and a sample optical cavity configured to support a sample optical resonance and comprising: a sample cavity; and a second pair of mirrors, different from the first pair of mirrors, and comprising: one of the first mirrors; and one of the second mirrors, such that the second pair of mirrors is opposingly arranged to one another, and the sample cavity is interposed between the second pair of mirrors.

Additionally disclosed is a system to determine a pressure of an analyte gas, the system comprising: an article comprising: a substrate; a reference optical cavity disposed on the substrate and comprising a reference cavity interposed between a first pair of mirrors, the reference optical cavity being configured to support a reference optical resonance and to receive a reference gas disposed in the reference cavity; and a sample optical cavity disposed on the substrate and comprising a sample cavity interposed between a second pair of mirrors, the sample optical cavity being configured to support a sample optical resonance and to receive a sample gas disposed in the sample cavity; a sample gas source in gas communication with the sample optical cavity to provide the sample gas; and a null detector in gas communication with an analyte gas source and the sample gas source, the null detector configured to produce a response to a difference in pressure between the analyte gas and sample gas.

Further additionally disclosed is a process for determining a sample condition, the process comprising: introducing a reference light to a reference cavity; adjusting the reference light to the reference cavity; transmitting the reference light from the reference cavity; introducing a sample light to a sample cavity; adjusting the sample light to the sample cavity; transmitting the sample light from the sample cavity; detecting the sample light; providing feedback for locking the reference light to the reference cavity; providing feedback for locking the sample light to the sample cavity; combining the reference light with the sample light; detecting a beat frequency, based on the reference light and the sample light; and determining a sample condition, based on the beat frequency.

Also disclosed is a process for determining a sample condition, the process comprising: introducing a reference light to a reference cavity; adjusting the reference light to the reference cavity; transmitting the reference light from the reference cavity; introducing a sample light to a sample cavity; adjusting the sample light to the sample cavity; transmitting the sample light from the sample cavity; detecting the sample light; providing feedback for locking the reference light to the reference cavity; providing feedback for locking the sample light to the sample cavity; combining the reference light from the reference cavity with the sample light from the sample cavity; detecting a beat frequency, based on the reference light in the sample light; and determining a sample condition comprising a pressure of the sample gas, a temperature of the sample gas, or a refractive index of the sample gas.

BRIEF DESCRIPTION OF THE DRAWINGS

The following descriptions should not be considered limiting in any way. With reference to the accompanying drawings, like elements are numbered alike:

FIGS. 2A, 2B, and 2C respectively show a longitudinal cross-section, transverse cross-section along line B-B, and end view of an embodiment of an article;

FIGS. 3A, 3B, and 3C respectively show a longitudinal cross-section, transverse cross-section along line C-C, and end view of an embodiment of an article;

FIGS. 4A, 4B, 4C, and 4D respectively show a longitudinal cross-section, transverse cross-section along line E-E, end view, and transverse cross-section along line D-D of an embodiment of an article;

FIGS. 5A, 5B, 5C, and 5D respectively show a longitudinal cross-section, transverse cross-section along line E3-E3, end view, and transverse cross-section along line D2-D2 of an embodiment of an article;

FIGS. 8A, 8B, 8C, 8D, 8E, 8F, 8G, and 8H respectively show a perspective view (8A), side view (8B), transverse cross-section along line H1-H1 (8C), end view (8D), longitudinal cross-section along line H2-H2 (8E), top view (8F), longitudinal cross-section along line I1-I1 (8G), and longitudinal cross-section along line I2-I2 (8H) of an embodiment of an article;

DETAILED DESCRIPTION

A detailed description of one or more embodiments is presented herein by way of exemplification and not limitation.

It has been discovered that an article herein provides a photonic-based determination of a sample condition such as pressure, temperature, or refractive index. The article is highly sensitive, temporally stable, and responsive over a range of temperature, pressure, or refractive index to be determined.

As used herein, "gas" (e.g., sample gas, reference gas, analyte gas) can be a pure gas where a chemical species of the gas is known or can be ascertained, a gas composition that includes a plurality of gases, and the like. The gas can be monatomic or polyatomic. Moreover, although gas (e.g., sample gas, reference gas, analyte gas, secondary sample gas, and the like) is used in certain embodiments, it should be appreciated that the gas can be substituted by a liquid (e.g., hydrophobic liquid, hydrophilic liquid, liquid composition, pure liquid) or a combination of a liquid and a gas. The liquid can be selected to transmit a laser beam, e.g., a sample laser beam, a reference laser beam, and the like.

Figure 1A:
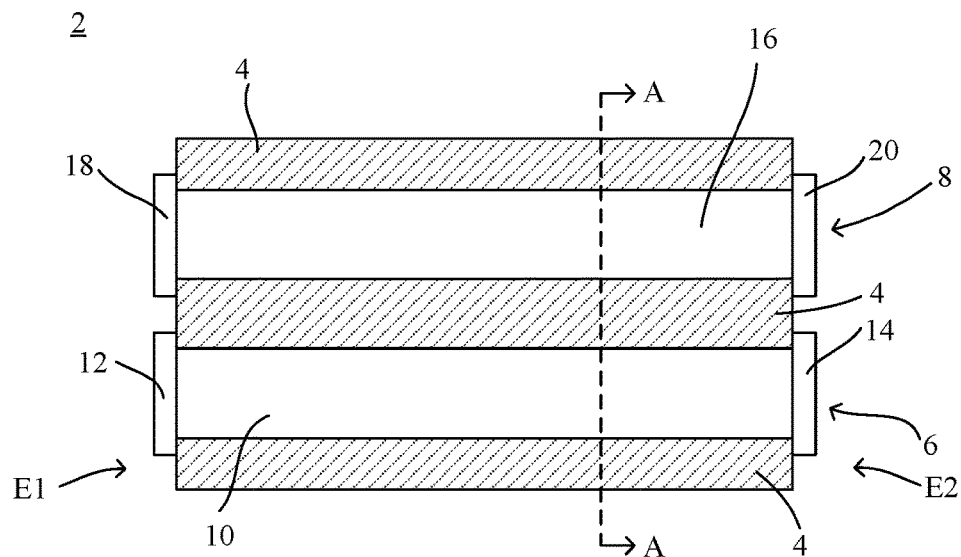
FIGS. 1A, 1B, and 1C respectively show a longitudinal cross-section, transverse cross-section along line A-A, and end view of an embodiment of an article.
Figure 1B:
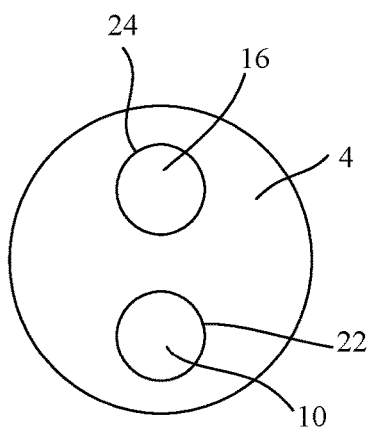
Figure 1C:
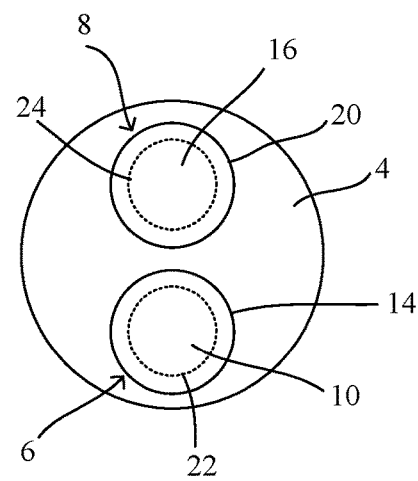

In an embodiment, as shown in FIG. 1A (longitudinal cross-section), FIG. 1B (transverse cross-section along line A-A shown in FIG. 1A), and FIG. 1C (end view of second end E2), article 2 includes substrate 4 in which reference optical cavity 6 and sample optical cavity 8 are disposed. Reference optical cavity 6 includes reference cavity 10 interposed between first reference cavity mirror 12 disposed at first end E1 and second reference cavity mirror 14 disposed at second end E2. Sample optical cavity 8 includes sample cavity 16 interposed between first sample cavity mirror 18 disposed at first end E1 and second sample cavity mirror 20 disposed at second end E2. According to an embodiment, sample cavity 16 and reference cavity 10 have axial lengths that independently traverse an entire length of substrate 4, a portion of the length of substrate 4 or combination thereof.

Here, reference cavity 10 is bounded by reference cavity wall 22. Sample cavity 16 is bounded by sample cavity wall 24. Although not shown, a sample gas communication path to communicate a sample gas to sample cavity 16 or to evacuate sample cavity 16 can be included in substrate 4. Although not shown, a reference gas communication path to communicate a reference gas to reference cavity 10 or to evacuate reference cavity 10 can be included in substrate 4.

Further, a first pair of mirrors includes first reference cavity mirror 12 and second reference cavity mirror 14, wherein first reference cavity mirror 12 opposes second reference cavity mirror 14 on substrate 4. A second pair of mirrors includes first sample cavity mirror 18 and second sample cavity mirror 20, wherein first sample cavity mirror 18 and second sample cavity mirror 20 on substrate 4. In an embodiment, reference optical cavity 6 is configured to receive a reference gas disposed in reference cavity 10 and interposed between first reference cavity mirror 12 and second reference cavity mirror 14. According to an embodiment, sample optical cavity 8 is configured to receive a sample gas disposed in sample cavity 16 and interposed between first sample cavity mirror 18 and second sample cavity mirror 20.

It is contemplated that reference optical cavity 6 is leak tight or has an insignificant leak rate with respect to transmission of gas into or out of reference cavity 10, except for selected introduction to or removal of reference gas from reference cavity 10. It is further contemplated that sample optical cavity 8 is leak tight or has an insignificant leak rate with respect to transmission of gas into or out of sample cavity 16, except for selected introduction to or removal of sample gas from the sample cavity 16. In some embodiments, first reference cavity mirror 12, second reference cavity mirror 14, first sample cavity mirror 18, and second sample cavity mirror 20 are independently adhered to (e.g., by chemical (e.g., an adhesive or chemical bonding), physical, or mechanical (e.g., a fastener) adherence), formed from, or monolithically formed with substrate 4.

According to an embodiment, as shown in FIG. 2A (longitudinal cross-section), FIG. 2B (transverse cross-section along line B-B shown in FIG. 2A), and FIG. 2C (end view of second end E2), article 2 includes substrate 4 in which reference optical cavity 6 and sample optical cavity 8 are disposed. Reference optical cavity 6 includes reference cavity 10 interposed between first reference cavity mirror 12 disposed at first end E1 and second reference cavity mirror 14 disposed at second end E2. Sample optical cavity 8 includes sample cavity 16 interposed between first sample cavity mirror 18 disposed at first end E1 and second sample cavity mirror 20 disposed at second end E2. According to an embodiment, sample cavity 16 and reference cavity 10 have axial lengths that independently traverse an entire length of substrate 4, a portion of the length of substrate 4 or combination thereof. Here, sample cavity 16 is disposed on an external surface of substrate 4, whereas reference cavity 10 disposed in substrate 4 such that reference cavity 10 and sample cavity 16 are both disposed on substrate 4. Additionally, first sample cavity mirror 18 and second sample cavity mirror 20 are disposed on substrate 4 such that a portion of each of these mirrors overlap a portion of substrate 4 and sample cavity 16. In some embodiments, for example a monolithic structure of article 2, first sample cavity mirror 18 and second sample cavity mirror 20 extend from substrate 4 to overlap with sample cavity 16 in sample optical cavity 8, wherein first and second sample cavity mirrors (18, 20) and substrate 4 are a single monolithic member.

According to an embodiment, as shown in FIG. 3A (longitudinal cross-section), FIG. 3B (transverse cross-section along line C-C shown in FIG. 3A), and FIG. 3C (end view of second end E2), article 2 includes substrate 4 in which reference optical cavity 6 and sample optical cavity 8 are disposed. Reference optical cavity 6 includes reference cavity 10 interposed between first reference cavity mirror 12 disposed at first end E1 and second reference cavity mirror 14 disposed at second end E2. Sample optical cavity 8 includes sample cavity 16 interposed between first sample cavity mirror 18 disposed at first end E1 and second sample cavity mirror 20 disposed at second end E2. Here, sample cavity 16 is disposed on an external surface of substrate 4, whereas reference cavity 10 disposed in substrate 4 such that reference cavity 10 and sample cavity 16 are both disposed on substrate 4. Additionally, sample cavity wall 24 bounds a portion of sample cavity 16 to be partially disposed in substrate 4, and a portion of sample cavity 16 is not bounded by sample cavity wall 24.

A transverse cross-sectional shape of sample cavity wall 24 or reference cavity wall 22 (e.g., as shown in FIG. 1C, 2C, or 3C) independently can be any shape effective to support respectively the sample optical resonance or the reference optical resonance. Exemplary transverse cross-sectional shapes include a circular shape, elliptical shape, polygonal shape, and the like.

A transverse cross-sectional shape of substrate 4 can be any shape effective to support the sample optical resonance and the reference optical resonance as well as to provide introduction or evacuation of the sample gas, reference gas, or analyte gas from article 2. Exemplary transverse cross-sectional shapes include a circular shape, elliptical shape, polygonal shape, and the like.

In an embodiment, as shown in FIG. 4A (longitudinal cross-section), FIG. 4B (transverse cross-section along line E-E shown in FIG. 4A), FIG. 4C (end view of second end E2) and FIG. 4D (transverse cross-section along line D-D shown in FIG. 4A), article 2 includes substrate 4 in which reference optical cavity 6 and sample optical cavity 8 are disposed. Reference optical cavity 6 includes reference cavity 10 interposed between first reference cavity mirror 12 disposed at first end E1 and second reference cavity mirror 14 disposed at second end E2. Sample optical cavity 8 includes sample cavity 16 interposed between first sample cavity mirror 18 disposed at first end E1 and second sample cavity mirror 20 disposed at second end E2. Article 2 further includes reference gas path 26 in fluid communication with reference cavity 10 to communicate reference gas to or from reference cavity 10.

In some embodiments, as shown in FIG. 5A (longitudinal cross-section), FIG. 5B (transverse cross-section along line E3-E3 shown in FIG. 5A), FIG. 5C (end view of second end E2) and FIG. 5D (transverse cross-section along line D2-D2 shown in FIG. 5A), article 2 includes substrate 4 in which reference optical cavity 6 and sample optical cavity 8 are disposed. Reference optical cavity 6 includes reference cavity 10 interposed between first reference cavity mirror 12 disposed at first end E1 and second reference cavity mirror 14 disposed at second end E2. Sample optical cavity 8 includes sample cavity 16 interposed between first sample cavity mirror 18 disposed at first end E1 and second sample cavity mirror 20 disposed at second end E2. Article 2 further includes secondary sample optical cavity 30 disposed on substrate 4. Secondary sample optical cavity 30 includes secondary sample cavity 32 bounded by secondary sample cavity wall 34 and interposed between secondary sample cavity mirrors 36a (primary mirror) and 36b (secondary mirror). Secondary gas path 38 is in fluid communication with secondary cavity 32 to communicate secondary gas to or from secondary cavity 32. Here, sample cavity 16 is disposed externally on substrate 4.

Figure 6A:
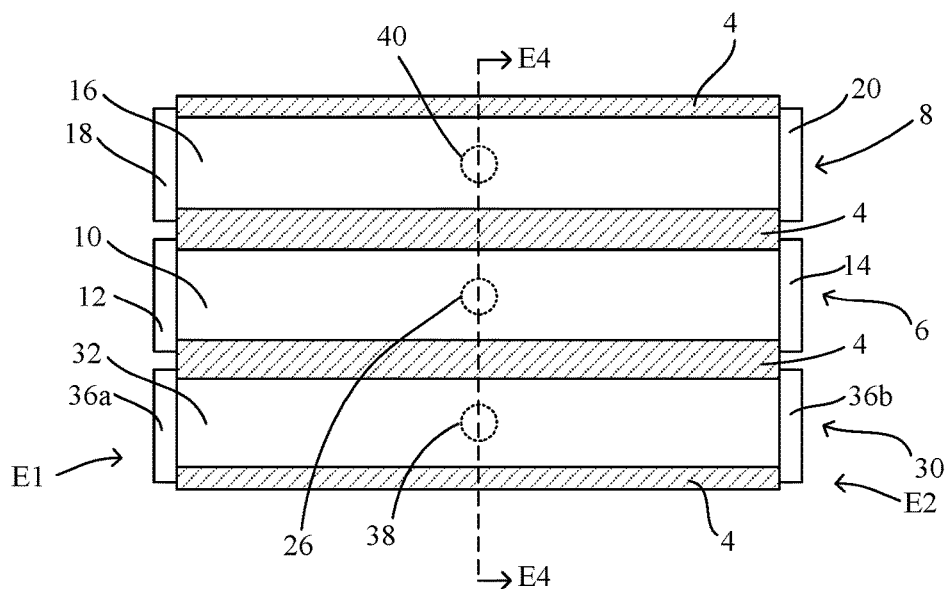
FIGS. 6A, 6B, and 6C respectively show a longitudinal cross-section, transverse cross-section along line E4-E4, and end view of an embodiment of an article.
Figure 6B:
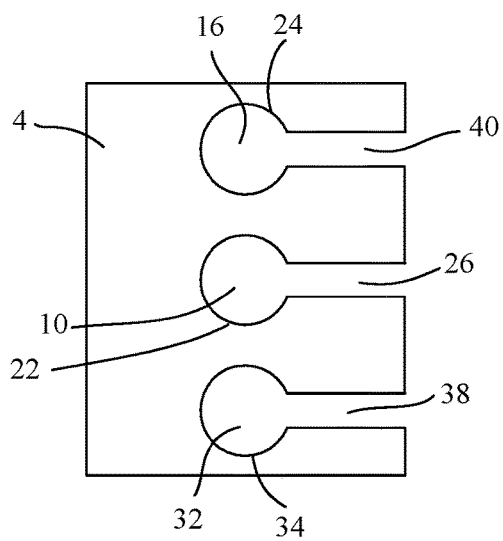
Figure 6C:
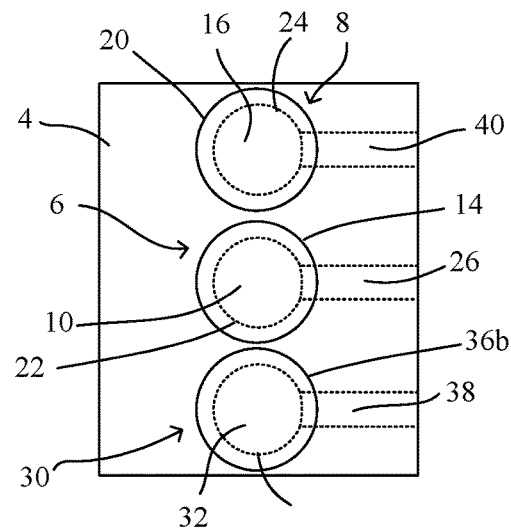

In some embodiments, sample cavity 30, reference cavity 10, and secondary sample cavity 32 are disposed in substrate 4 as shown in FIG. 6A (longitudinal cross-section), FIG. 6B (transverse cross-section along line E4-E4 shown in FIG. 6A), and FIG. 6C (end view of second end E2). Here, sample gas path 40, reference gas path 26, and secondary gas path 38 respectively are in gas communication with sample cavity 16, reference cavity 10, and secondary cavity 32 to communicate their widths respectively sample gas, reference gas, and secondary gas.

Figure 7A:
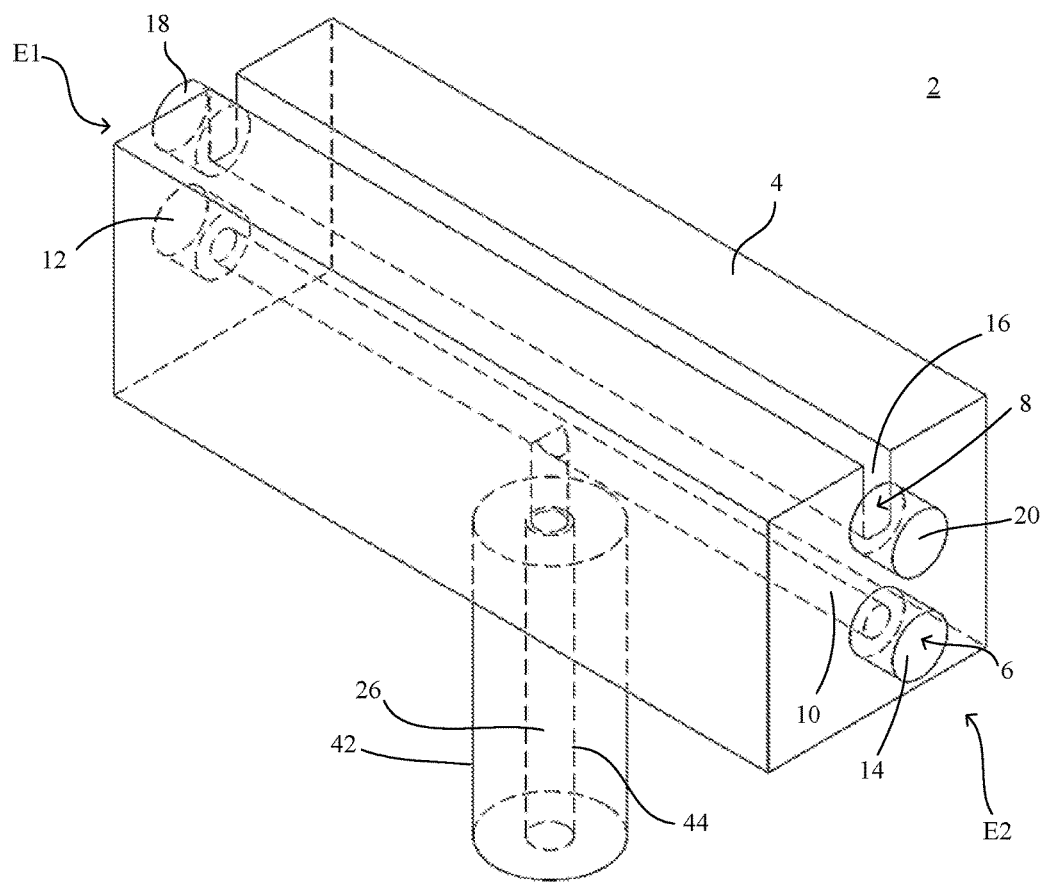
FIGS. 7A, 7B, 7C, 7D, 7E, and 7F respectively show a perspective view (7A), top view (7B), end view (7C), longitudinal cross-section along line F-F (7D), side view (7E), and transverse cross-section along line G-G (7F) of an embodiment of an article.
Figure 7B:
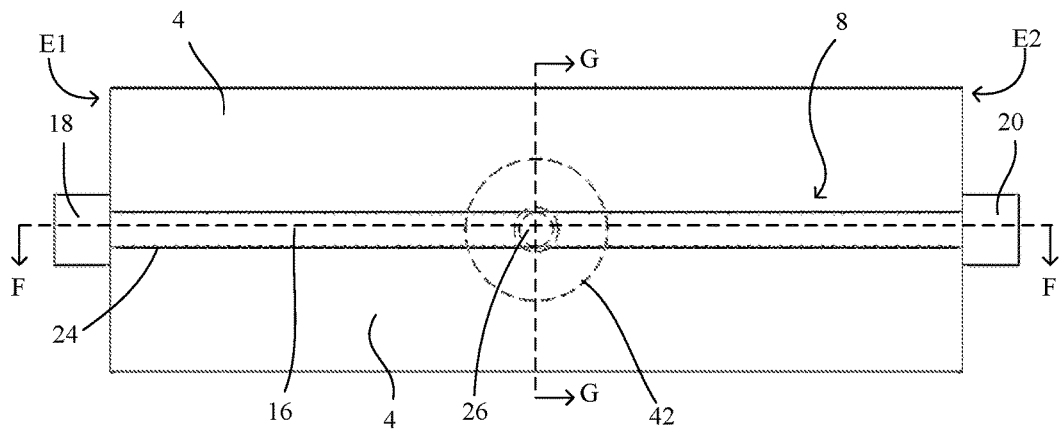
Figure 7C:
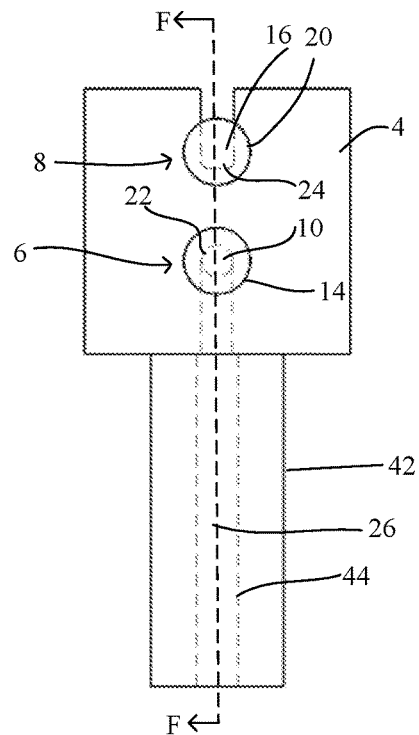
Figure 7D:
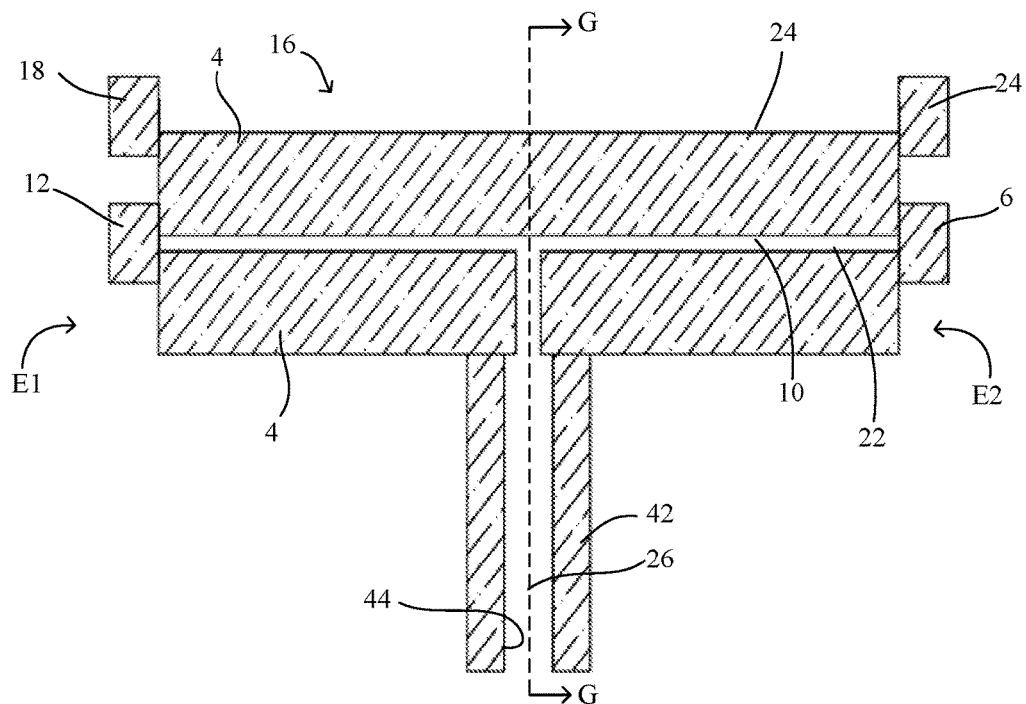
Figure 7E:
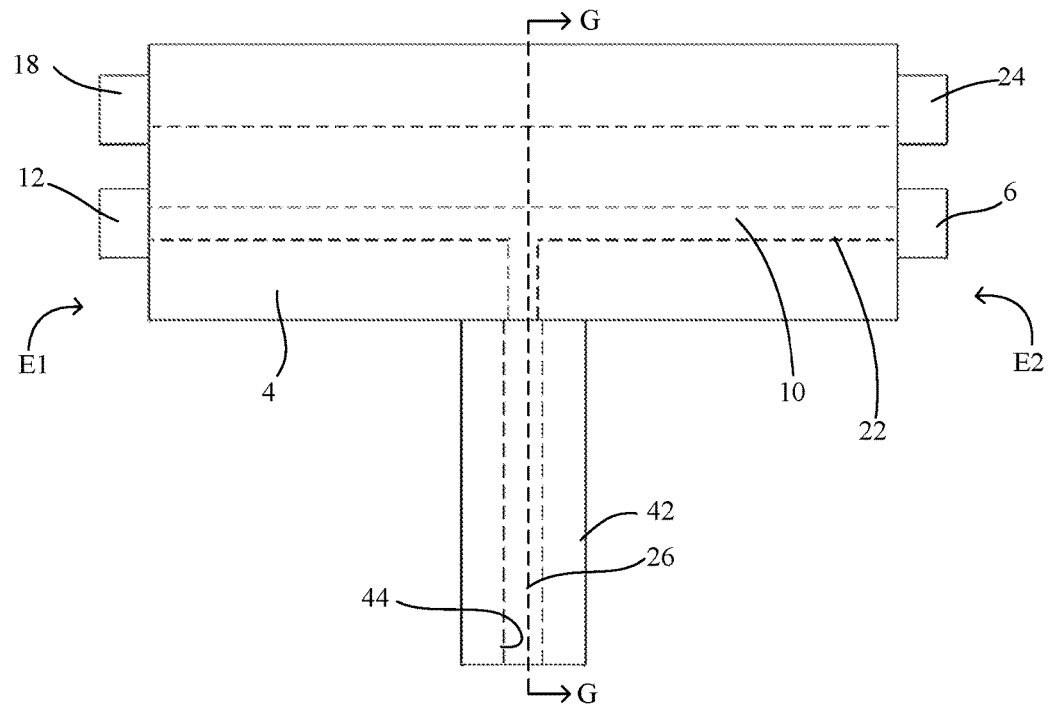
Figure 7F:
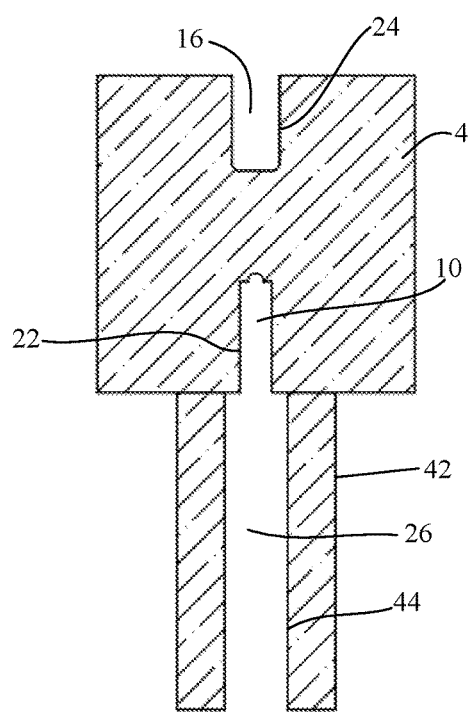

It is contemplated that a coupling member, e.g., reference cover 42 is shown in FIG. 7A, can be independently attached to and provide gas communication with sample cavity 16, reference cavity 10, or secondary cavity 32. With reference to article 2 shown in a perspective view (FIG. 7A), top view (FIG. 7B), end view (FIG. 7C), longitudinal cross-section along line F-F (FIG. 7D), side view (FIG. 7E), and transverse cross-section along line G-G (FIG. 7F), reference coupler 42 is disposed on substrate 4 and extends from a surface of substrate 4. Reference coupler 42 includes reference gas path 26 in gas communication with reference cavity 10, and reference coupler inner wall 44 bounds reference gas path 26. An angle between a longitudinal axis of reference coupler 42 and a longitudinal axis of substrate 4 or reference cavity 10 can be any angle effective to communicate reference gas between reference gas path 26 and reference cavity 10, e.g., an orthogonal angle, obtuse angle, or acute angle.

Figure 8A:
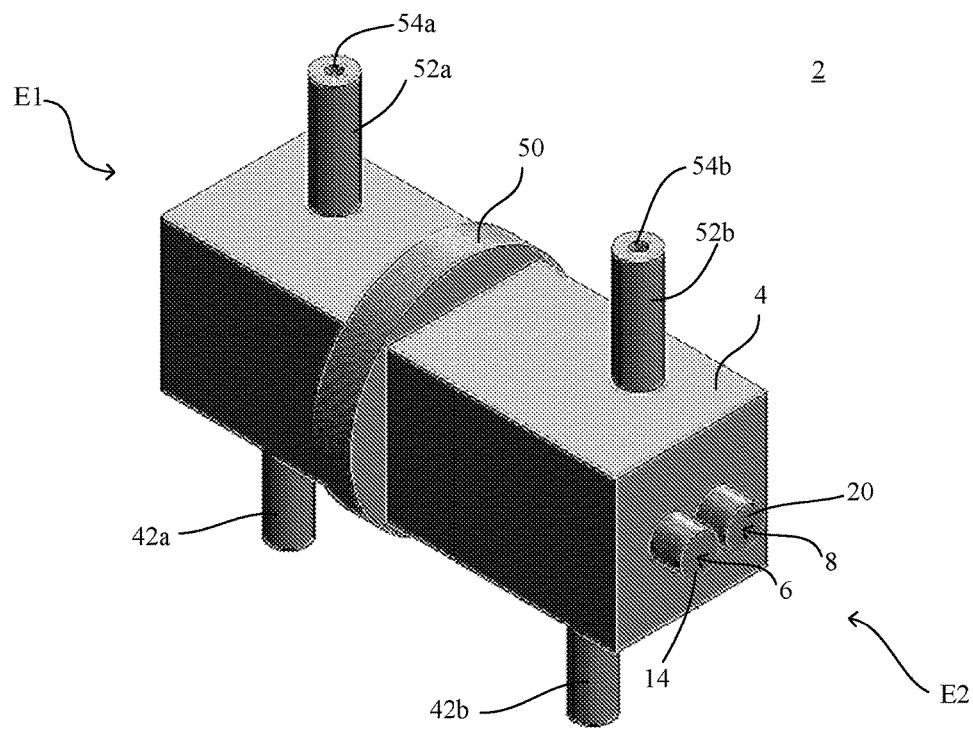
Figure 8B:
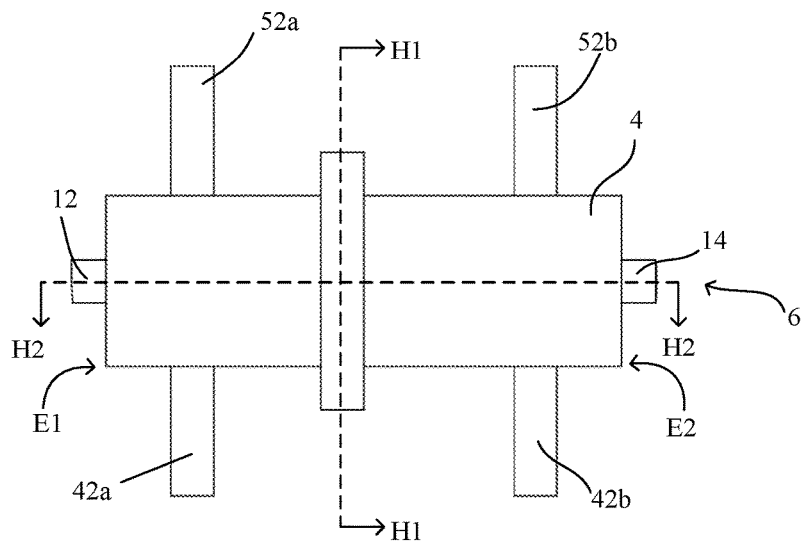
Figure 8C:
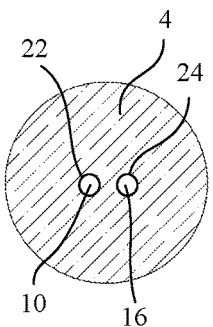
Figure 8D:
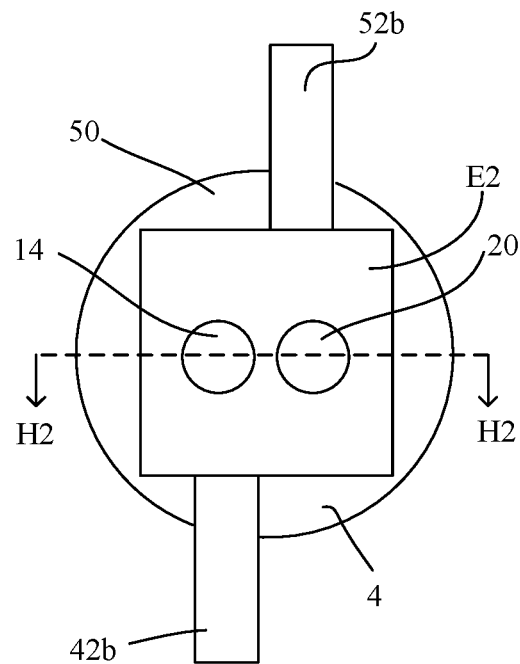
Figure 8E:
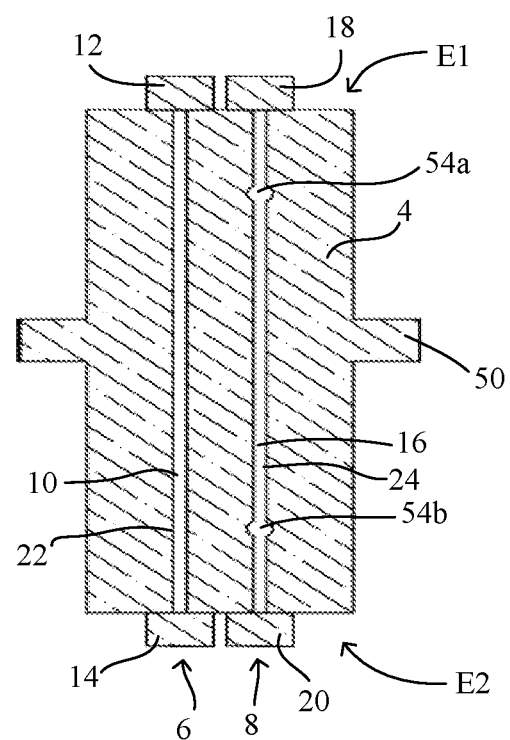

In some embodiments as shown in figures FIG. 8A (perspective view), FIG. 8B (side view), FIG. 8C (transverse cross-section along line H1-H1), FIG. 8D (end view), FIG. 8E (longitudinal cross-section along line H2-H2), FIG. 8F (top view), FIG. 8G (longitudinal cross-section along line I1-I1), and FIG. 8H (longitudinal cross-section along line I2-I2), article 2 includes intermediate member 50 disposed about substrate 4. Intermediate member 50 and substrate 4 can be a same material (e.g., ultra-low expansion quartz) or a different material. Further, intermediate member 50 and substrate 4 can be a can be a monolithic structure or bonded together. Additionally, article 2 includes reference gas paths 26a, 26b (see FIG. 8G) respectively disposed in reference couplers 42a, 42b and sample gas path 54a, 54b (see FIG. 8H) disposed in sample couplers 52a, 52b. Reference gas paths 26a, 26b are in gas communication with reference cavity 10. Similarly, sample gas path 54a, 54b are in gas communication with gas cavity 16. Moreover, reference gas paths 26a, 26b and sample gas path 54a, 54b respectively provide reference gas and sample gas to respectively flow in reference cavity 10 and sample cavity 16. It is contemplated that article 2 can be disposed an mounted in an exterior container by contacting intermediate member 50 with the container without contacting substrate 4. In some embodiments, a portion of substrate 4 or intermediate member 50 can be in contact with the container for mounting article 2 therein.

With respect to embodiments shown in FIGS. 1A, 1B, 1C, 2A, 2B, 2C, 3A, 3B, 3C, 4A, 4B, 4C, 4D, 5A, 5B, 5C, 5D, 6A, 6B, 6C, 7A, 7B, 7C, 7D, 7E, 7F, 8A, 8B, 8C, 8D, 8E, 8F, 8G, and 8H, article 2 include substrate 4 configured to maintain an axial length of sample cavity 16, to maintain an axial length of reference cavity 10, or to maintain an axial length of secondary sample cavity 32. As used here, axial length refers to a length of a cavity that extends from first end E1 to second end E2 as opposed to a transverse length (which would be at an angle, e.g., perpendicular, to the axial length) or radial length (which would also be at an angle, e.g., perpendicular, to the axial length). In some embodiments, an axial direction of reference cavity 10 and an axial direction of sample cavity 16 are arranged substantially parallel. Accordingly, sample cavity 16, reference cavity 10, or secondary sample cavity 32 have a length that is fixed to the substrate so a dimensional change (e.g., contraction or expansion) of substrate 4 would similarly change a length of sample cavity 16, reference cavity 10, or secondary sample cavity 32. In some embodiments, substrate 4 includes a material that does not substantially change in a length dimension or has an ultra-low thermal expansion, based on a change in a length dimension with temperature of substrate 4. Accordingly, in some embodiments, article 2 has a fixed length of sample cavity 16, reference cavity 10, or secondary sample cavity 32.

Figure 9A:
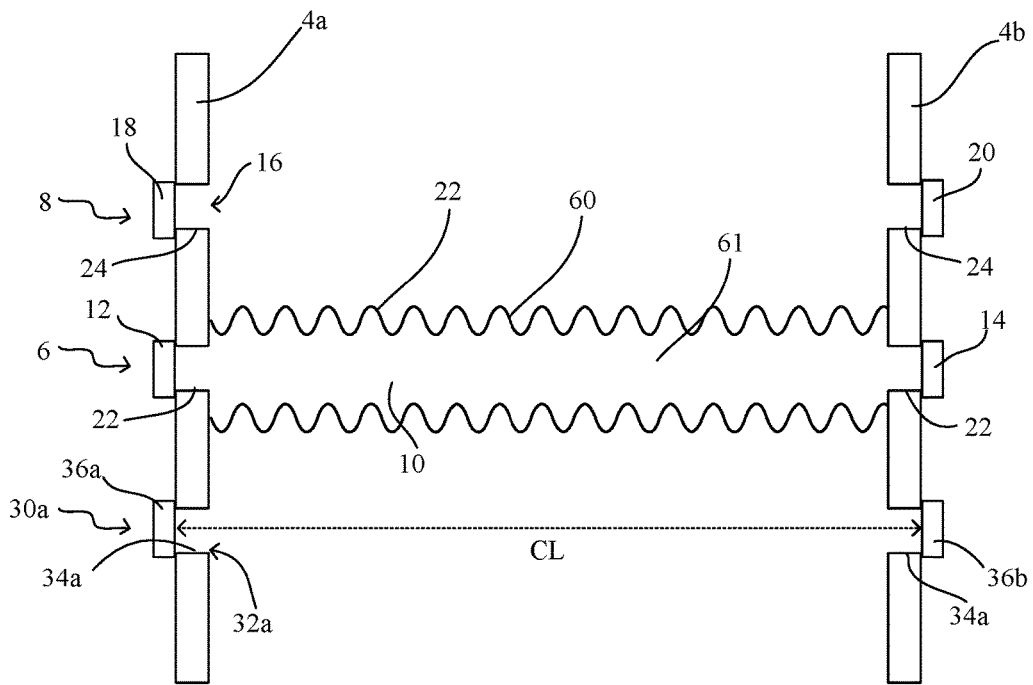
FIGS. 9A and 9B respectively show a longitudinal cross-section and end view of an embodiment of an article.
Figure 9B:
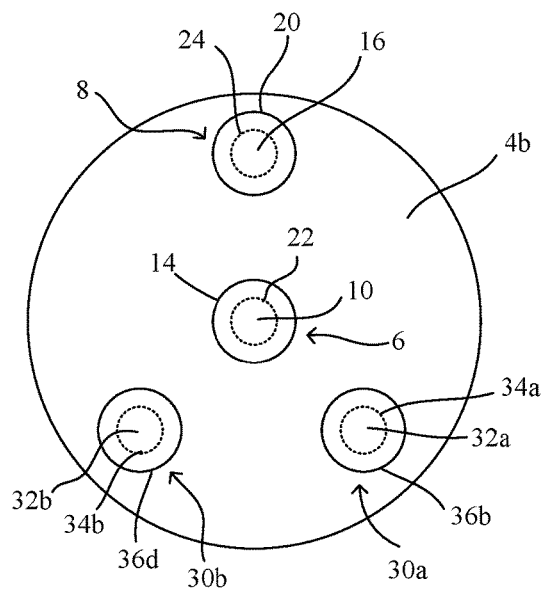

In some embodiments, as shown in FIGS. 9A (longitudinal cross-section) and 9B (end view of second end E2), article 2 has a variable length of sample cavity 16, reference cavity 10, or secondary sample cavity 32. Here, article 2 includes first substrate 4a and second substrate 4b spaced apart from first substrate 4a and opposingly disposed to first substrate 4a. A plurality of first mirrors (18, 12, 36a) are disposed on first substrate 4a. A plurality of second mirrors (20, 14, 26b) are disposed on second substrate 4b such that a plurality of pairs of mirrors (e.g., first pair (18, 20), second pair (12, 14), third pair (36a, 36b)) are present, and each mirror in the respective pair of mirrors opposes one another. Article 2 further includes variable length member 60 interposed between first substrate 4a and second substrate 4b. Variable length member 60 has internal hollow portion 61 disposed therein. Article 2 includes reference optical cavity 6 that is configured to support a reference optical resonance. Reference optical cavity 6 includes reference cavity 10 and a first pair of mirrors. The first pair of mirrors includes first mirror 12 and second mirror 14 such that mirrors (12, 14) are arranged opposing one another, and reference cavity 10 is interposed between the first pair of mirrors and includes internal hollow portion 61. Sample optical cavity 8 is also included in article 2 and is configured to support a sample optical resonance and includes sample cavity 8 and a second pairs of mirrors that is different from the first pair of mirrors. The second pair of mirrors includes first mirrors 18 and second mirror 20 such that the mirrors (18, 20) in the second pair of mirrors are arranged opposing one another, and sample cavity 16 is interposed between the second pair of mirrors. In some embodiments, article 2 having a variable length of cavities (16, 10, 32) also includes secondary sample optical cavities (30b, 30a) that respectively include secondary sample cavities (32a, 32b) respectively bounded by secondary sample cavity wall (34a, 34b) and interposed between a pair of secondary sample cavity mirrors (36a, 36b; or 36c, 36d). Here, the cavities (16, 10, 32) have a variable length indicated as cavity length CL, the length of which is selected at an arbitrary value by positioning first substrate 4a at an selected arbitrary position with respect to second substrate 4b.

To achieve selected arbitrary positioning and a variable length of cavities (16, 10, 32), first substrate 4a can be attached to first positioning member 62, and second substrate 4b can be attached to second positioning member 64. First positioning member 62 and second positioning member 64 can independently move first substrate 4a relative to second substrate 4b. Exemplary first and second positioning members (62, 64) include linear stages and the like. Since cavity length CL is selectively variable. A distance between the second substrate 62 and first substrate 60 is likewise variable such that a length of variable length member 60 changes with respect to relative positioning of first substrate 4a and second substrate 4b. Exemplary variable length members 60 include bellows, reciprocating sleeved tubes (e.g., see FIG. 11, first tube 60a and second tube 60b), and the like. It is contemplated that variable length member 60 is leak tight or substantially leak free to sustain a selected pressure in internal hollow portion 61.

Figure 10:
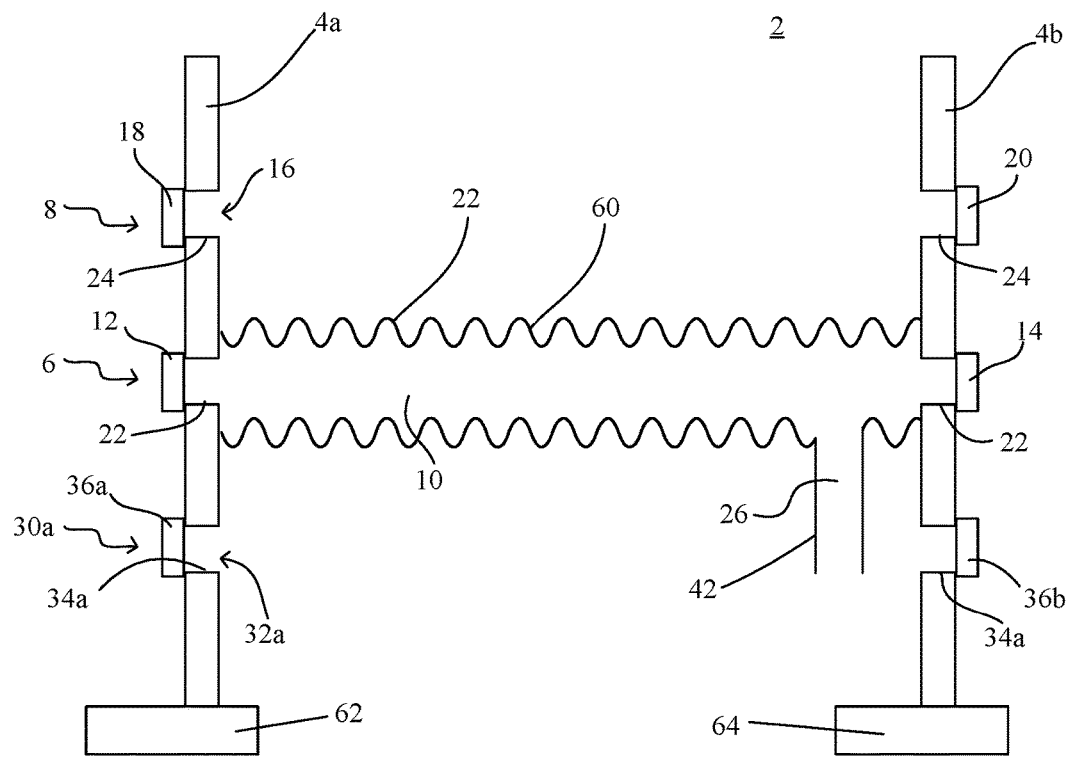
FIG. 10 shows a longitudinal cross-sectional of the article shown in FIG. 9A in contact with positioning members.

According to an embodiment, as shown in FIG. 10 (longitudinal cross-section), article 2 includes first substrate 4A connected to first positioning member 62 and second substrate 4b connected to second positioning member 64. Further, article 2 also includes reference coupler 42 and reference gas path 26 in gas communication with reference cavity 10.

Figure 11:
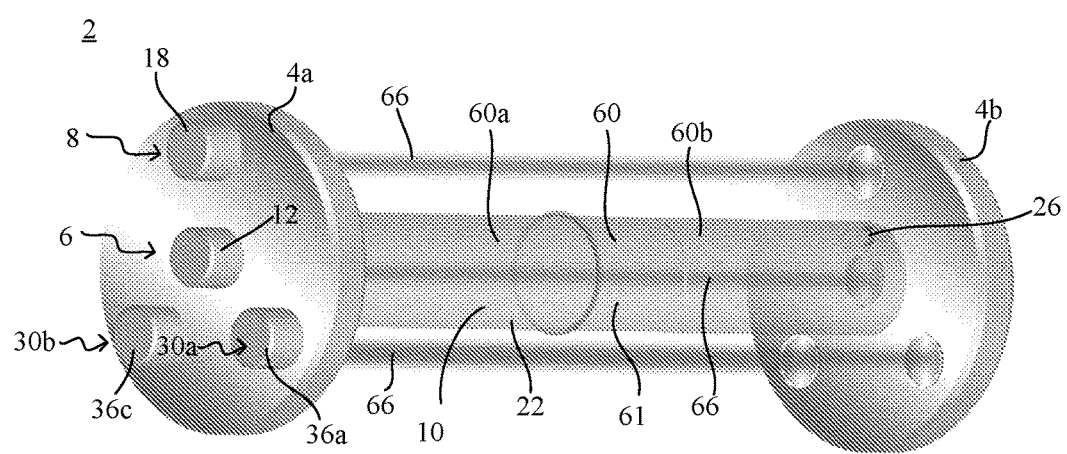
FIG. 11 shows a perspective view of an embodiment of an article.

As shown in FIG. 11 (perspective view), article 2 includes variable length member 60 that includes a pair of reciprocating tubes, first tube 60a in sliding engagement with second tube 60b to form overlapping portion 61. First tube 60a and second tube 60b can be a same or different material, e.g., glass, metal, polymer, and the like. Overlapping portion 61 can include a dynamic seal such as ground glass, O-ring, lubricant (e.g., vacuum grease, molybdenum disulfide, and the like), and the like. Here, variable length member 60 and first and second substrates (4a, 4b) may be a same or different material such that cavity length CL can be selected and maintained.

In an embodiment, article 2 includes first substrate 4a, second substrate 4b spaced apart from first substrate 4a and opposingly disposed to first substrate 4a, a plurality of first mirrors disposed on first substrate 4a, a plurality of second mirrors disposed on second substrate 4b, variable length member 60 interposed between first substrate 4a and second substrate 4b and including internal hollow portion 61, and reference optical cavity 6 configured to support a reference optical resonance. Reference optical cavity 6 includes reference cavity 10 and a first pair of mirrors that includes one of the first mirrors and one of the second mirrors, such that the first pair of mirrors is opposingly arranged to one another, and reference cavity 10 is interposed between the first pair of mirrors and includes internal hollow portion 61. Article 2 further includes sample optical cavity 8 that is configured to support a sample optical resonance and includes sample cavity 16 and a second pair of mirrors, different from the first pair of mirrors, and that includes one of the first mirrors and one of the second mirrors, such that the second pair of mirrors is opposingly arranged to one another, and sample cavity 16 is interposed between the second pair of mirrors. Here, a length of sample cavity 16 is selectively adjustable, and a length of reference cavity 10 is selectively adjustable. Moreover, reference optical cavity 6 is configured to receive a reference gas disposed in reference cavity 10 and interposed between first pair of mirrors. Sample optical cavity 8 is configured to receive a sample gas disposed in sample cavity 16 and interposed between the second pair of mirrors. Article 2 further includes reference gas path 26 in gas communication with reference cavity 10 and configured to provide the reference gas to reference optical cavity 6. Sample gas path 54 is in gas communication with sample cavity 16 and configured to provide the sample gas to sample optical cavity 8. Article 2 also further includes a secondary sample optical cavity that includes a secondary sample cavity, a third pair of mirrors (e.g., including one of the first mirrors and one of the second mirrors, such that the third pair of mirrors is opposingly arranged to one another, and the secondary sample cavity is interposed between the third pair of mirrors), wherein the secondary sample optical cavity is configured to receive a secondary sample gas disposed in the secondary sample cavity and interposed between the third pair of mirrors.

Figure 12A:
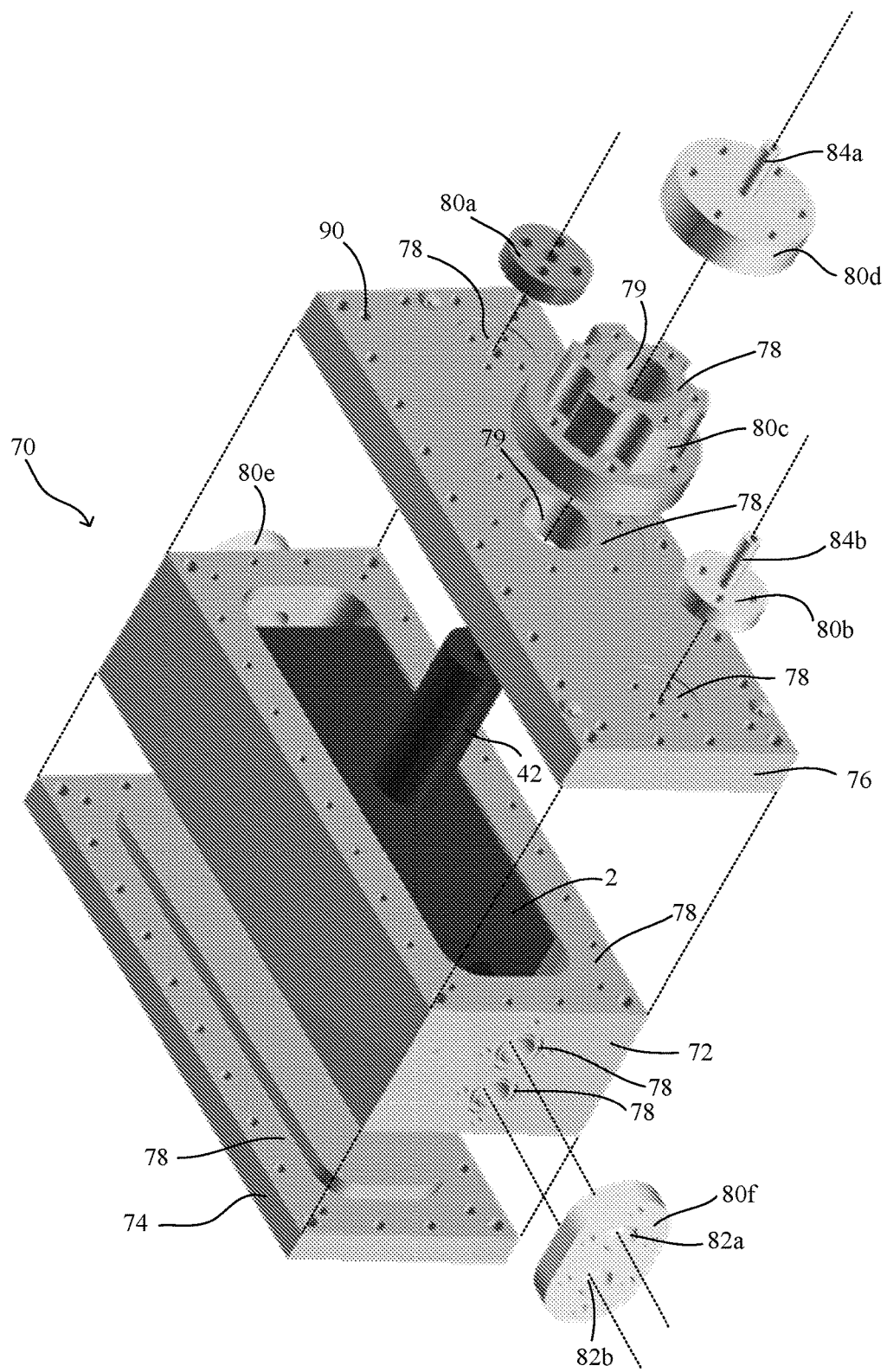
FIGS. 12A, 12B, and 12C respectively show an exploded view, cutaway perspective view, cutaway side view of an embodiment of an article.
Figure 12B:
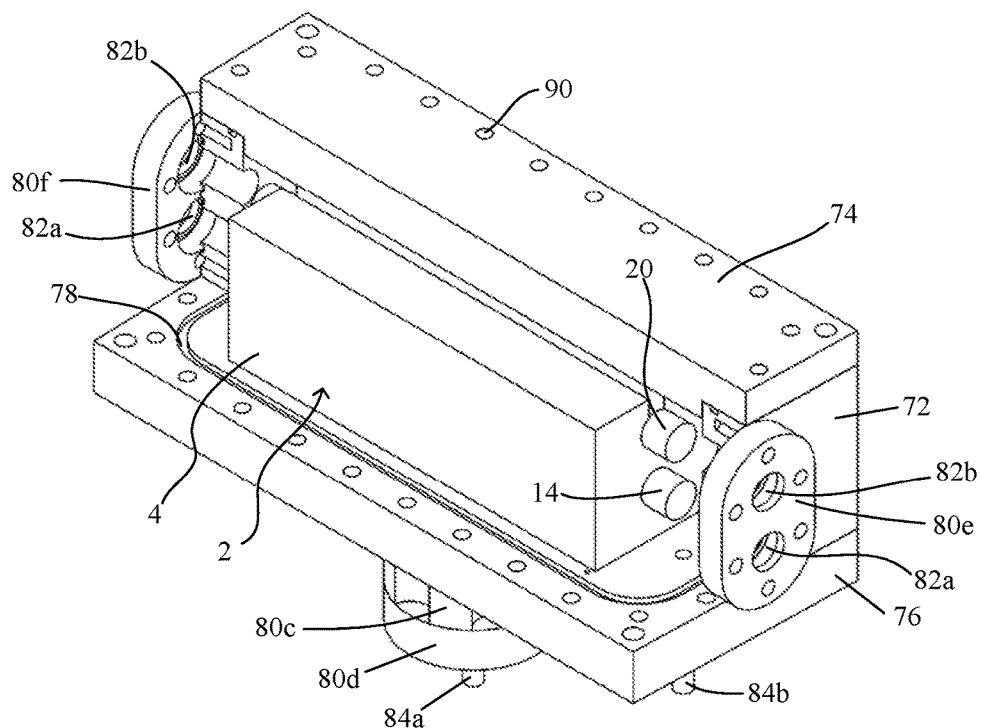
Figure 12C:
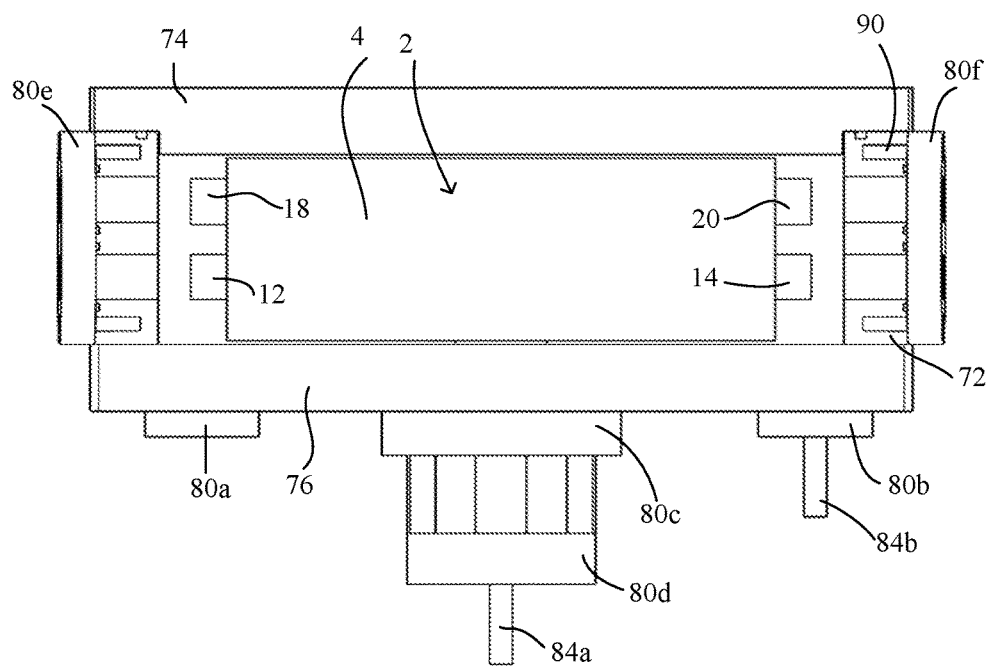

According to an embodiment, article 2 can be enclosed in a container to control environmental conditions subject to article 2. Exemplary environmental conditions include temperature, pressure, and the like. With reference to FIGS. 12A (exploded view), 12B (cutaway perspective view), and 12C (cutaway side view), article 2 is disposed in a container 70. Container 70 includes various elements that allow control over environmental conditions to which article 2 is subjected and also includes optical access and gas communication to various parts of article 2 from external gas sources, vacuum regulation equipment, or vacuum pumps. Here, container 70 includes central enclosure 72, first lid 74, and second lid 76, which are sealingly engaged at sealing surface 78 (e.g., a gasket or O-ring gland) and can be connected to one another by a fastener (e.g., a bolt, screw, and the like) disposed in or through hole 90 distributed throughout portions of enclosure 72, first lid 74, and second lid 76. Optical flanges 80e and 80f are disposed on central enclosure 72 and provide optical access to article 2 via optical ports 82a, 82b on which can be disposed optical windows (not shown) for transmission of light, e.g., laser light. Reference coupler 42 of article 2 is received by feedthrough 79 of second lid 76 and flange 80c and is in sealing communication with flange 80d such that reference gas port 84a communicates reference gas through reference gas path 26 (partially visible in FIG. 12A) without reference gas leaking into an area between article 2 and central enclosure 72. Flange 80a is disposed on second fluid 76 to provide gas communication with internal portion of central enclosure 72 such that container 70 can be evacuated, vented, or filled with a selected gas. Additionally, flange 80b is disposed on the second lid 76 and includes sample gas port 84b to provide gas communication of sample gas to or from sample cavity 16.

In an embodiment of article 2, substrate 4, first substrate 4a, and second substrate 4b can be a material with an ultralow coefficient of thermal expansion. Exemplary materials include sapphire, quartz, glass, ceramic, and the like. Low expansion glass include low expansion glass and low expansion crystallized glass, such as synthetic quartz glass containing $TiO_2$, ULE (trademark: Corning Cord 7972), ZERODUR (trademark of Schott A. G.), and the like. Likewise, synthetic quartz glass containing $TiO_2$ is an ultralow expansion glass.

In some embodiments, article 2 is disposed in container 70. Container 70 can be made of a material selected for high thermal conductivity or high thermal insulation. Exemplary materials for container 70 include metals such as copper (including oxygen free high connectivity copper), stainless steel, aluminum, nickel, alloys, and the like; glass; composites (e.g., fiberglass, polymer composites and, the like); and the like.

Mirrors (e.g., first sample cavity mirror 18, second sample cavity mirror 20, secondary sample cavity mirror 36a, 36b) independently can be made of materials used for substrate 4, first substrate 4a, or second substrate 4b. The material for the mirrors independently can be selected to transmit a wavelength of incident laser light into an optical cavity (e.g., reference optical cavity 6, sample optical cavity 8, secondary sample optical cavity 30) and transmit a wavelength of light after such laser light passes through a gas (e.g., sample gas, reference gas, secondary sample gas, analyte gas) in the optical cavity (e.g., reference optical cavity 6, sample optical cavity 8, secondary sample optical cavity 30).

In article 2 that includes variable length member 60, variable length member 60 can be, e.g., a bellows, reciprocating tubes, and the like. The bellows can be a metallic bellows such as an edge-welded bellows, hydraulically formed bellows, and the like. A reciprocating to can include material such as metal, glass, ceramic, polymer, and the like.

Also described herein or various gases such as a sample gas, reference gas, analyte gas, secondary sample gas, and the like. Such gases independently can be an arbitrary gas. The composition of such gas can be known or unknown. Without limitation, exemplary gases include atomic gases, diatomic gases, polyatomic gases, or a combination thereof. The gas can be pure or substantially pure, or the gas can be a composition. Moreover, the gas can be stable or reactive, e.g., in an electronically excited state, metastable states, a radical state, and the like. In and embodiment, the sample gas is nitrogen, helium, air, and the like. In certain embodiments, the like gas is air, nitrogen, and the like. In a particular embodiment, the gas is selected to have a known refractive index or a refractive index that can be calculated from a theoretical or semi-empirical model, e.g., thermodynamics, statistical mechanics, classical mechanics, quantum mechanics, density functional theory, or a combination thereof. The gas can have an arbitrary water content, i.e., have an arbitrary humidity, based on a mole fraction of water present in the gas.

Figure 13A:
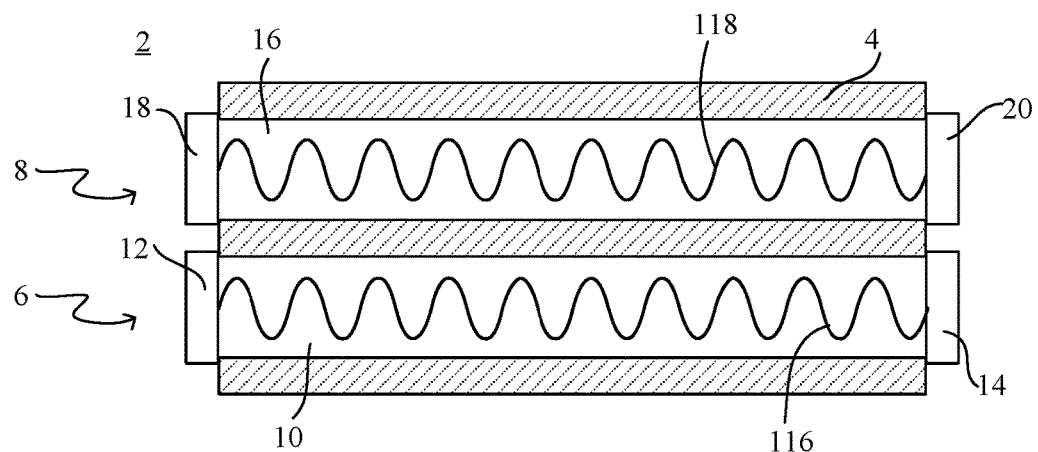
FIGS. 13A, 13B and 13C show a longitudinal cross-section of an embodiment of an article with a reference light and sample light.
Figure 13B:
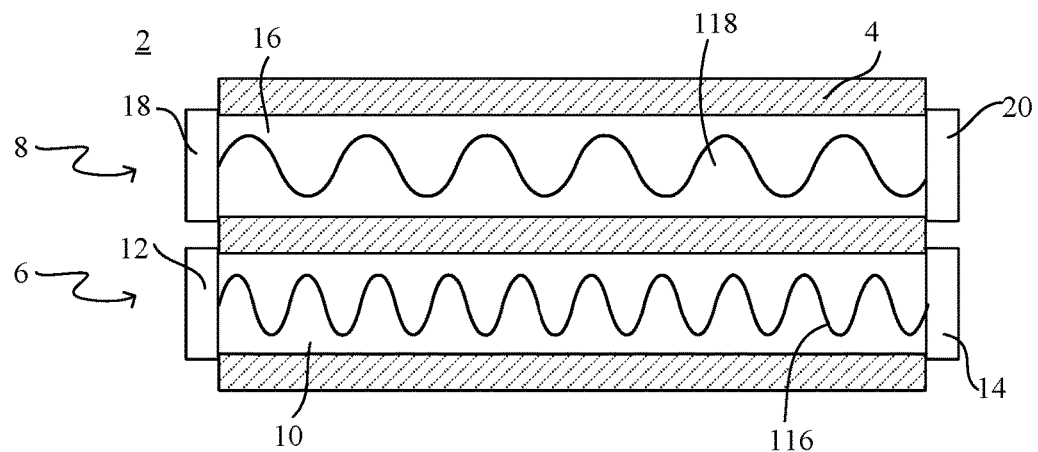
Figure 13C:
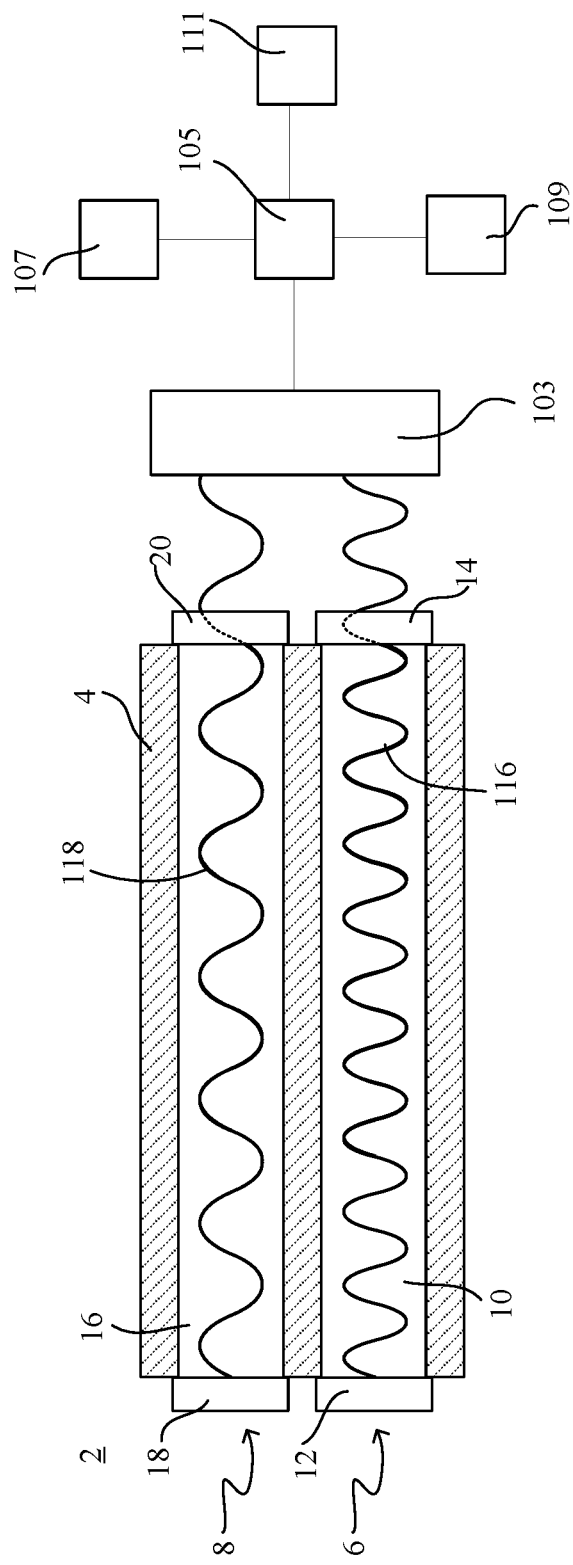
Figure 14A:
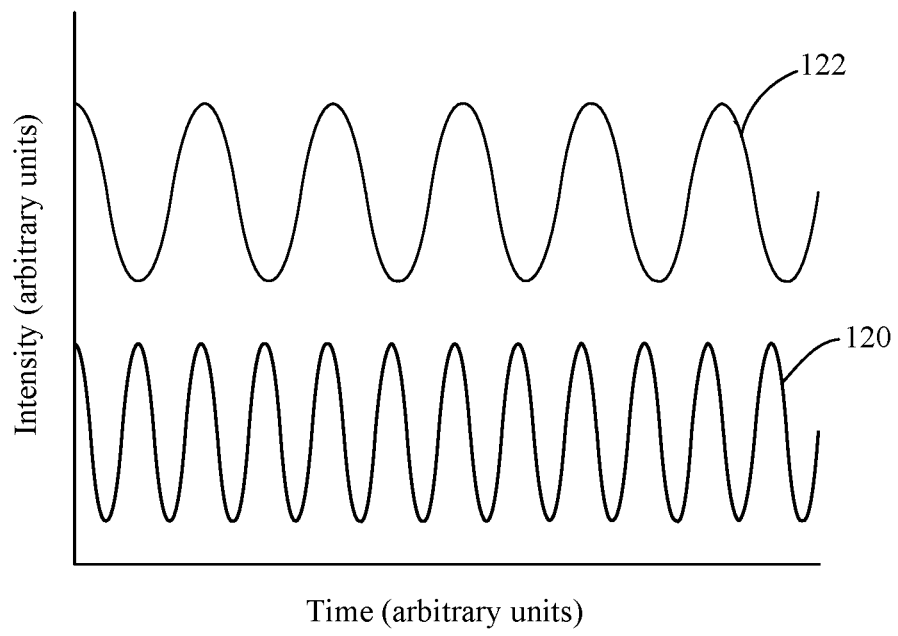
FIGS. 14A and 14B show graphs of intensity versus time.
Figure 14B:
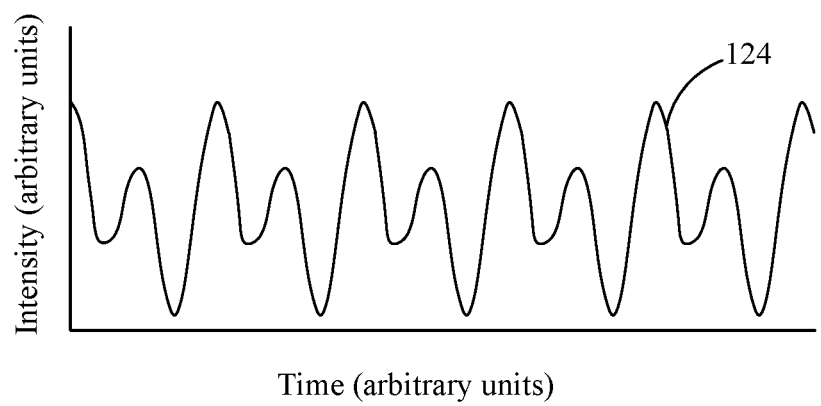

According to an embodiment, with reference to FIGS. 13A, 13B, 13C (which include longitudinal cross-section of article 2), in a process for determining a sample condition, article 2 is configured to have a vacuum in reference optical cavity 6 and sample optical cavity 8. Reference optical cavity 6 is configured to receive reference light 116, and sample optical cavity 8 is configured to receive sample light 118. Reference light 116 has a reference light frequency that can be locked to reference cavity 10 to produce a reference standing wave. Sample light when 18 has an first sample light frequency that can be a locked to sample cavity 16 to produce a sample standing wave. Thereafter, with reference to FIG. 13B, sample gas can be disposed in sample cavity 16. Since the sample gas has a different refractive index than that of the vacuum in sample cavity 16, a frequency of the sample light is changed in response to disposition of sample gas in sample cavity 16 from the first sample light frequency to a second sample light frequency, which can be locked to sample cavity 16 to form a standing wave. Upon producing standing waves in reference optical cavity 8 and sample optical cavity 6, reference light 116 and sample light 118 are respectively transmitted to a beam combiner 103 followed by a light detector 105. In response to receiving light, with reference to FIGS. 13C and 14A, the reference light detector 105 communicate a reference signal 120 and sample signal 122 to feedback circuitry 107 and 109 that is configured to lock light to sample cavity and reference cavity. A third output from 105 is a composite signal 24 (shown in FIG. 14B), i.e., a super position of reference light 116 and sample light 118), and to determine a sample condition of sample gas disposed in sample cavity 16, e.g., based a beat frequency present in composite signal 124. Further, such determination of a sample condition can be made in view of signals received by receiver detector 111 prior to disposal of sample gas 118 in sample cavity 16 while sample optical cavity 16 and reference optical cavity 10 were under vacuum. Exemplary sample conditions include temperature, pressure, refractive index, and the like. Here, the three signals can be distinguished by filtering in 107, 109, and 111. In another embodiment, light 116 and 118 is transmitted to individual detectors that feed 107 and 109 followed by sending the combined signal to 111. Furthermore, beat signal 111 could be detected by combining light 8 and light 6 using for example beam splitters prior to entering the cavity, which under some conditions will provide better signal detection with lower noise. Furthermore, the feedback signals to 107 and 109 can also be derived from reflected light at the entrance to the cavities (sample and reference) using for example Pound-Drever-Hall locking technique.

In a particular embodiment, article 2 is used to determine, e.g., pressure of the sample gas by detecting a difference in a wavelength of sample light resonating in sample optical cavity 16 filled with sample gas and a wavelength of the reference light resonating in reference optical cavity 10 that is under vacuum, or in some embodiments filled with a reference gas. A change in pressure of the sample gas in sample cavity 16 is a change in density of the sample gas, which results in a concomitant change (e.g., increasing or decreasing) the wavelength (or frequency when locked) of sample light resonating in sample optical cavity 16 while reference light in reference optical cavity 10 is unchanged because the reference gas is not subjected to a change in its pressure. In this manner, the difference in the wavelengths of sample light and reference light is used to determine sample condition, e.g., pressure the sample gas.

Figure 15:
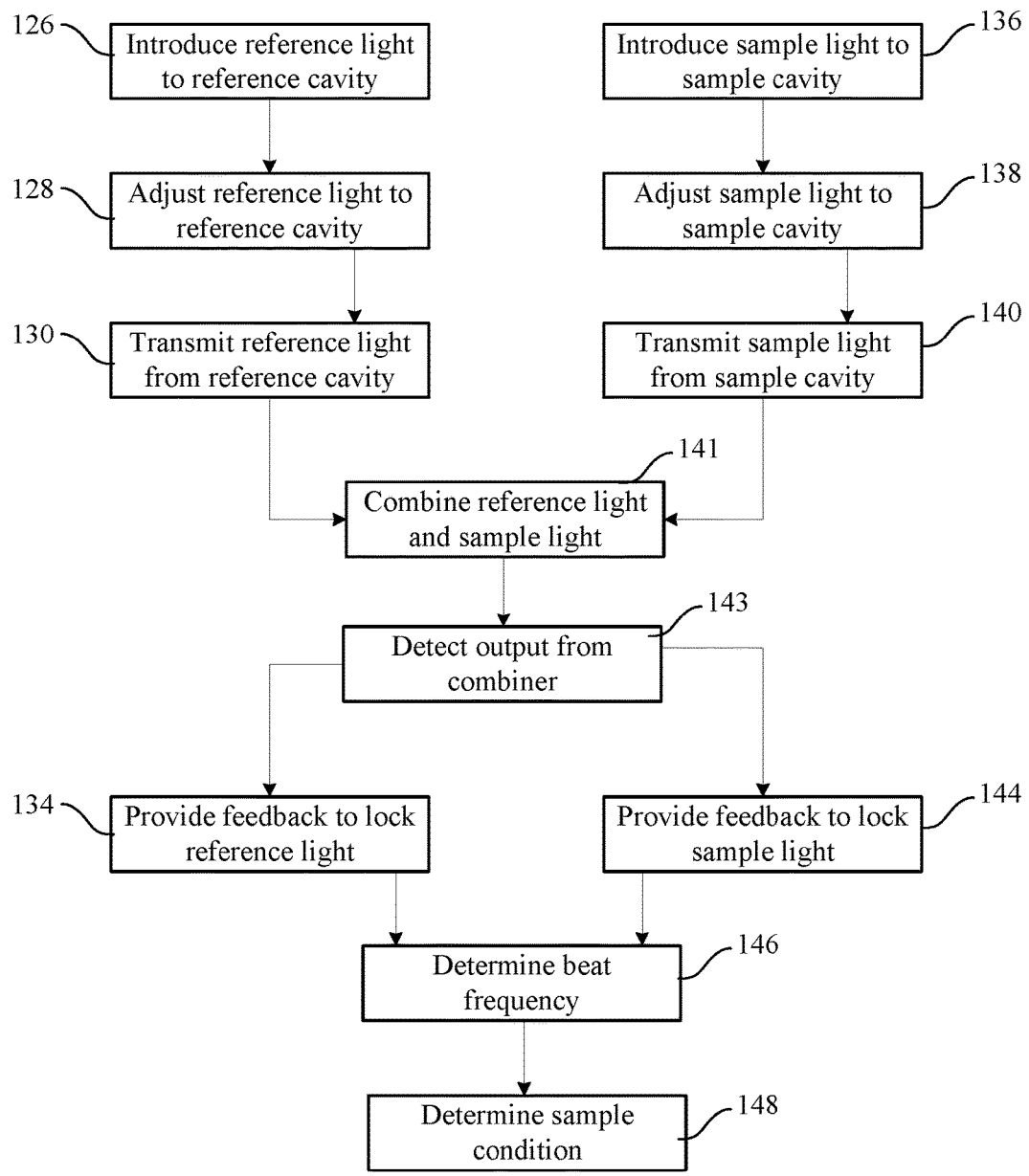
FIG. 15 shows a flowchart of an embodiment of a process for determining a sample condition.

In an embodiment, as shown in FIG. 15, a process for determining a sample condition includes providing article 2, optionally adjusting a pressure of reference gas (if present, otherwise adjusting a pressure of a gas) disposed in reference optical cavity 6, optionally adjusting a pressure of sample gas (if present, otherwise adjusting a pressure of a gas) disposed in sample optical cavity 8, introducing a reference light to reference cavity 10 (step 126), adjusting the reference light to reference cavity 10 (step 128), transmitting the reference light from reference cavity 10 (step 130), and disposing into a light combiner. The process also includes introducing a sample light to sample cavity 16 (step 136), adjusting the sample light to sample cavity 16 (step 138), transmitting the sample light from a sample cavity 16 (step 140), and disposing into a light combiner 141. Further, the light from the combiner is disposed onto a detector 143. Further, the process includes determining a beat frequency (step 146) of the reference light transmitted from reference optical cavity 6 and the sample light transmitted from a sample optical cavity 8. Based on the beat frequency, the process includes determining a sample condition (step 148).

Figure 16:
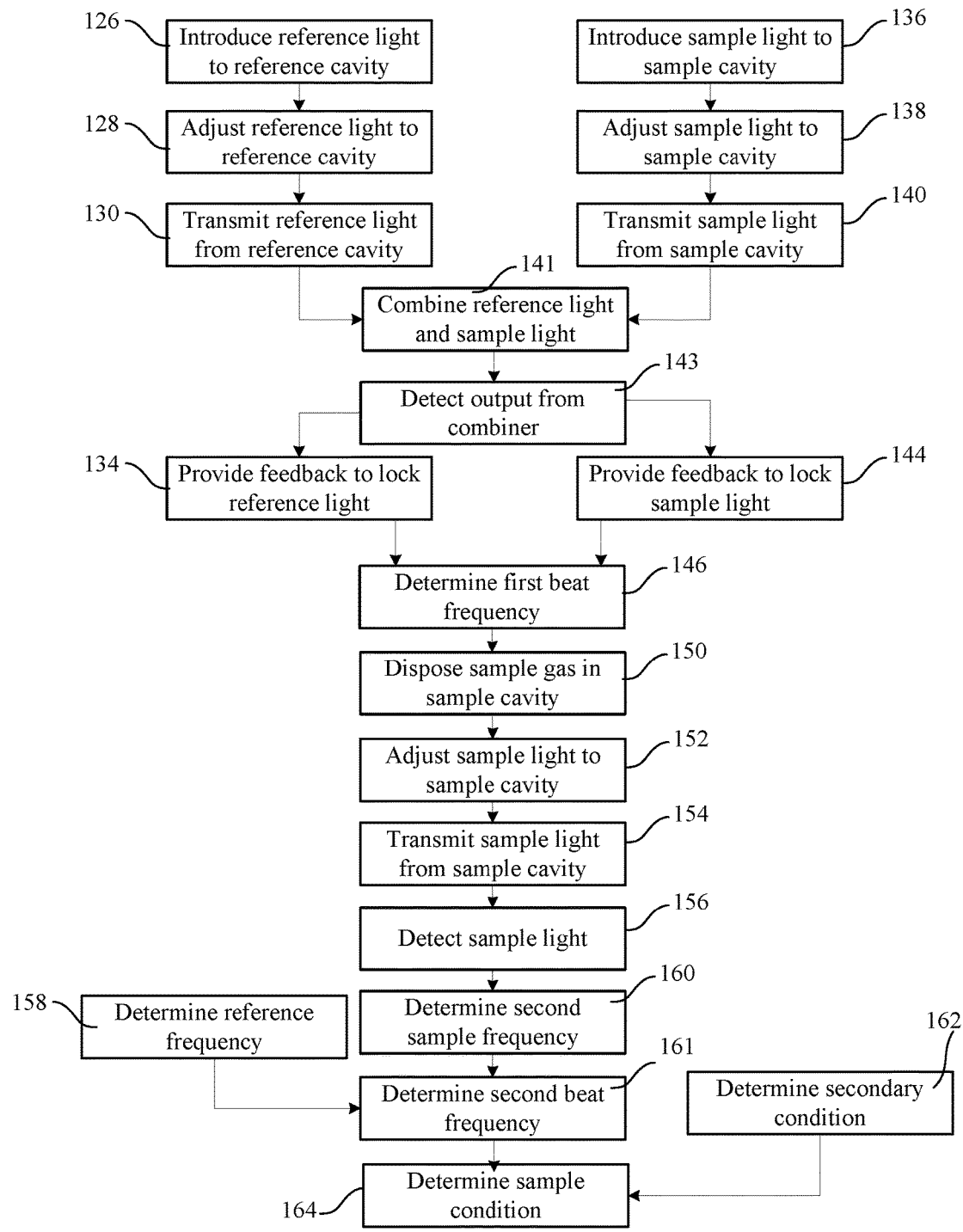
FIG. 16 shows a flowchart of an embodiment of a process for determining a sample condition.

According to an embodiment, as shown in FIG. 16, a process for determining a sample condition includes adjusting a pressure of reference gas (if present, otherwise adjusting a pressure of a gas) disposed in reference optical cavity 6, adjusting a pressure of sample gas (if present, otherwise adjusting a pressure of a gas) disposed in sample optical cavity 8, introducing a reference light to reference cavity 10 (step 126), adjusting the reference light to reference cavity 10 (step 128), transmitting the reference light from reference cavity 10 (step 130), and disposing into a light combiner 141. Further, the light from the combiner is disposed onto a detector 143. The process also includes introducing a sample light to sample cavity 16 (step 136), adjusting the sample light to sample cavity 16 (step 138), transmitting the sample light from a sample cavity 16 (step 140 and disposing into a light combiner 141. Further, the light from the combiner is disposed onto a detector 143 Further, the process includes determining a first beat frequency (step 146) of the reference light transmitted from reference optical cavity 6 and the sample light transmitted from a sample optical cavity 8, disposing a sample gas and sample cavity 16 (step 150), adjusting the sample light to sample cavity 16 (step 152), transmitting the sample light from sample cavity 16 (step 154), detecting the sample light transmitted from sample cavity 16 (step 156), determining a second sample frequency from the sample light (step 160), determining a frequency of the reference light transmitted by reference optical cavity 10 (step 158), determining a second beat frequency (step 161) based on the reference frequency (from step 158) and second sample frequency (from step 160), determining a secondary condition (step 162), and determining the sample condition from the second beat frequency from step 161 and the secondary condition from step 162.

Here, the sample condition includes a pressure of the sample gas, temperature of the sample gas, or refractive index of the sample gas. The secondary condition includes a pressure of the sample gas, temperature the sample gas, or refractive index of the sample gas. It is contemplated that a temperature of the sample gas and a temperature of substrate 4 (or substrate 4a or 4b, is applicable in article 2) or the same or substantially the same. It is also contemplated that sample gas and substrate 4 are in thermal equilibrium. In this manner, the secondary condition can be a temperature of substrate 4. In an embodiment, the temperature of substrate 4 can be determined by a secondary temperature sensor such as a contact device (e.g., a thermocouple, thermistor, RTD, thermometer, and the like), noncontact device (e.g., pyrometer and the like), or combination thereof. Similarly, the secondary condition can be determined by a secondary pressure sensor such as an ion gauge, thermocouple gauge, spinning rotor gauge, and the like.

Figure 17A:
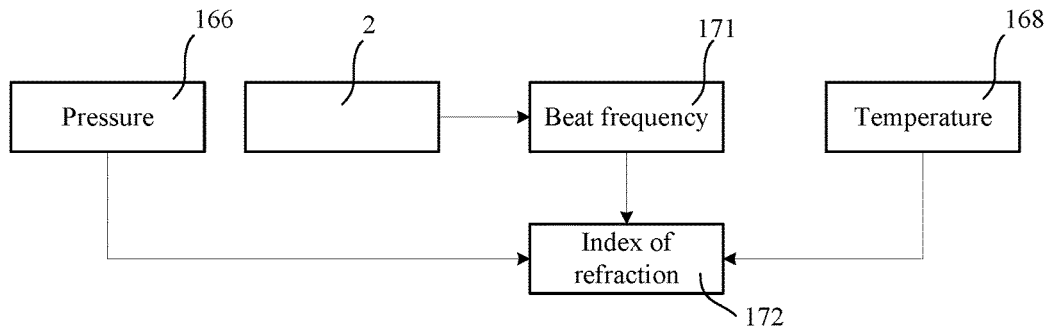
FIGS. 17A, 17B, 17C, and 17D respectively show representations for determining refractive index (17A), temperature (17B), pressure (17C), and Boltzmann's constant (17D)

In an embodiment, as shown in FIG. 17A, the beat frequency (labeled with reference numeral 171) determined from a difference in the frequencies of the reference light and sample light from article 2 is used to determine the index of refraction (labeled with reference numeral 172) of the sample gas disposed in sample cavity 16. Here, the beat frequency is used in combination with a secondary condition such as a pressure of the sample gas determined from secondary pressure sensor 166 or a temperature of the sample gas (or substrate 4 or in some embodiments container 70) determined from secondary temperature sensor 168.

Figure 17B:
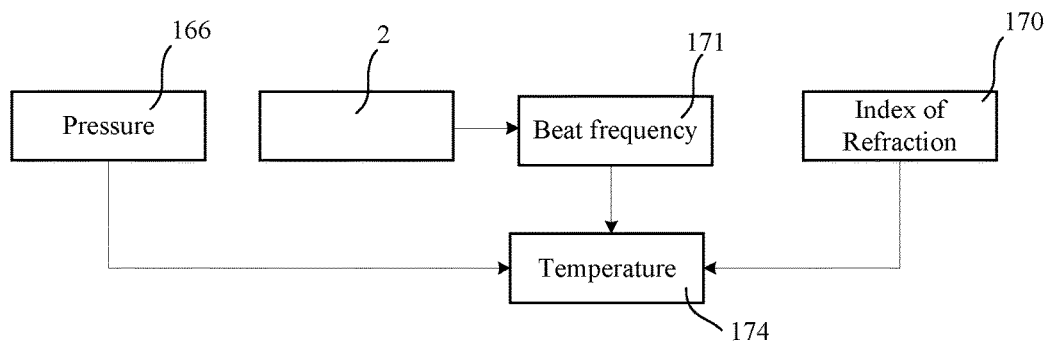

In some embodiments, as shown in FIG. 17B, the beat frequency (labeled with reference 171) determined from the difference in the frequencies of the reference light and sample light from article 2 is used to determine the temperature (labeled with reference numeral 174) of the sample gas disposed in sample cavity 16. Here, the beat frequency is used in combination with a secondary condition such as a pressure of the sample gas from a secondary pressure sensor 166 or refractive index (labeled with reference numeral 170) of the sample gas. The refractive index of the sample gas can be determined from theory or from previous measurements of molar refractive index.

Figure 17C:
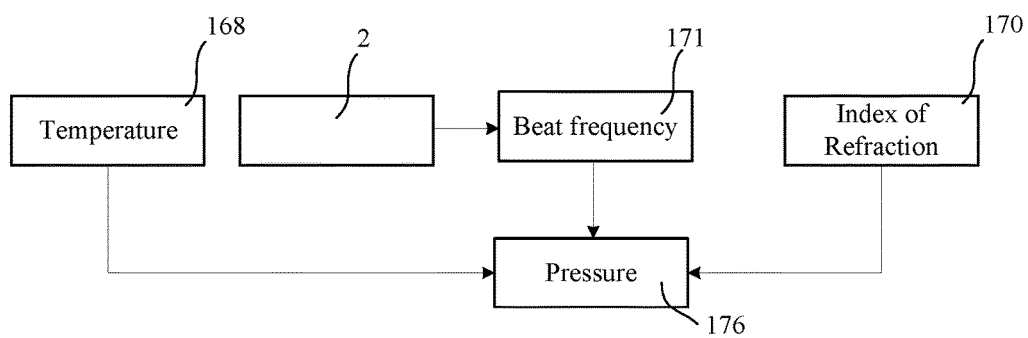

According to an embodiment, as shown in FIG. 17C, the beat frequency (labeled with reference 171) determined from the difference in the frequencies of the reference light and sample light from article 2 is used to determine the pressure (labeled with reference numeral 176) of the sample gas disposed in sample cavity 16. Here, the beat frequency is used in combination with a secondary condition such as a temperature of the sample gas from a secondary temperature sensor 168 or refractive index (labeled with reference numeral 170) of the sample gas. The refractive index of the sample gas can be determined from theory or from previous measurements of molar refractive index.

Figure 17D:
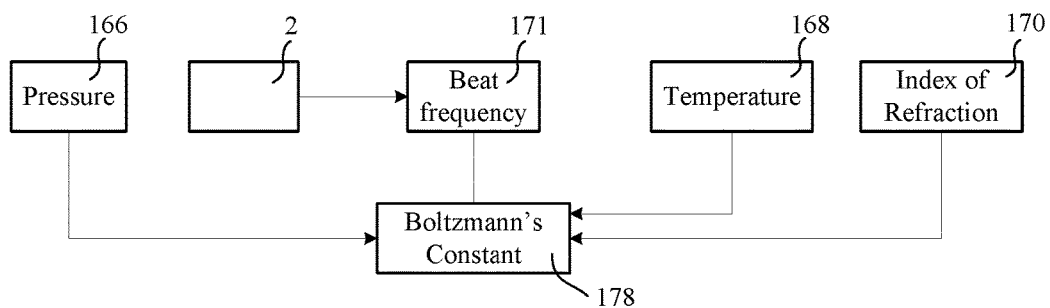

In some embodiments, as shown in FIG. 17D, the beat frequency (labeled with reference 171) determined from the difference in the frequencies of the reference light and sample light from article 2 is used to determine Boltzmann's constant (labeled with reference numeral 178). Here, the beat frequency is used in combination with a secondary condition such as a pressure of the sample gas from a secondary pressure sensor 166, refractive index (labeled with reference numeral 170) of the sample gas, or temperature of the sample gas from a secondary temperature sensor 168. The refractive index of the sample gas can be determined from ab initio theoretical quantum-chemistry calculations.

In other embodiments, the frequencies of the sample and reference light can be determined by comparison (beat frequency measurement) with a frequency-stabilized laser (examples include polarization stabilized laser, iodine stabilized laser, Zeeman stabilized laser).

Without wishing to be bound by theory, it is believed that the sample condition is related to the secondary condition in the following way. A Fabry-Pérot cavity can be used to determine pressure by measuring refractive index n or, equivalently, measuring the refractivity n−1. In a first approximation, the refractivity of a gas is simply proportional to the number density of molecules or to $P/(k_BT)$, where P is the pressure, $k_B$ is the Boltzmann constant and T temperature such that:

$$n-1 \propto P/(k_BT) \quad (1).$$

The proportionality is not exact equation (1) can be modified according to the Lorentz-Lorenz relation and to include virial coefficients to account for non-ideal gas behavior. The refractive index or refractivity can be determined through frequency measurements of laser light when a laser is servo-locked to a Fabry-Pérot cavity filled with nitrogen (or other gas) whose pressure is to be determined. The light transmitted through a Fabry-Pérot cavity is a maximum (in resonance) when the round-trip length of the cavity (2L) is an integer number, m, of laser wavelengths such that $$2L=m\lambda \quad (2).$$

Equation (2) does not include diffraction corrections and mirror phase shifts. The wavelength λ of light in the cavity depends on the speed c of light in a vacuum refractive index n of the gas in the cavity, and laser frequency f according to equation 3.

$$\lambda=c/nf \quad (3)$$

Combining (1) and (2) and solving for frequency gives $$f=mc/2nL \quad (4)$$

In an embodiment, frequency measurements are used to make measurements of the cavity length in vacuum or refractive index measurements of the gas in the cavity, and from equation (1) the refractive index measurement can be related to pressure. Consequently, measurements can be based on frequency metrology that provides high precision and accuracy. When the value for molar refractive index is calculated from ab inito quantum chemistry calculations, this provides a quantum-based primary pressure standard.

If pressure in the measurement cavity changes at constant temperature, causing n to change, the servo adjusts f to maintain resonance with the cavity. Equation (4) provides that a frequency change, df, is proportional to a change in refractive index, dn, or equivalently to d(n−1), which is proportional to pressure change, dP, such that:

$$df \propto dn = d(n-1) \propto dP \quad (5)$$

Exemplary light sources include a He—Ne laser with wavelength near 633 nm. They have a narrow frequency tuning range that may not track changes in refractive index. Consequently, a mode order m is changed to keep the laser frequency within its tuning range. Another exemplary light source includes tunable diode laser with a larger tuning range.

Figure 18:
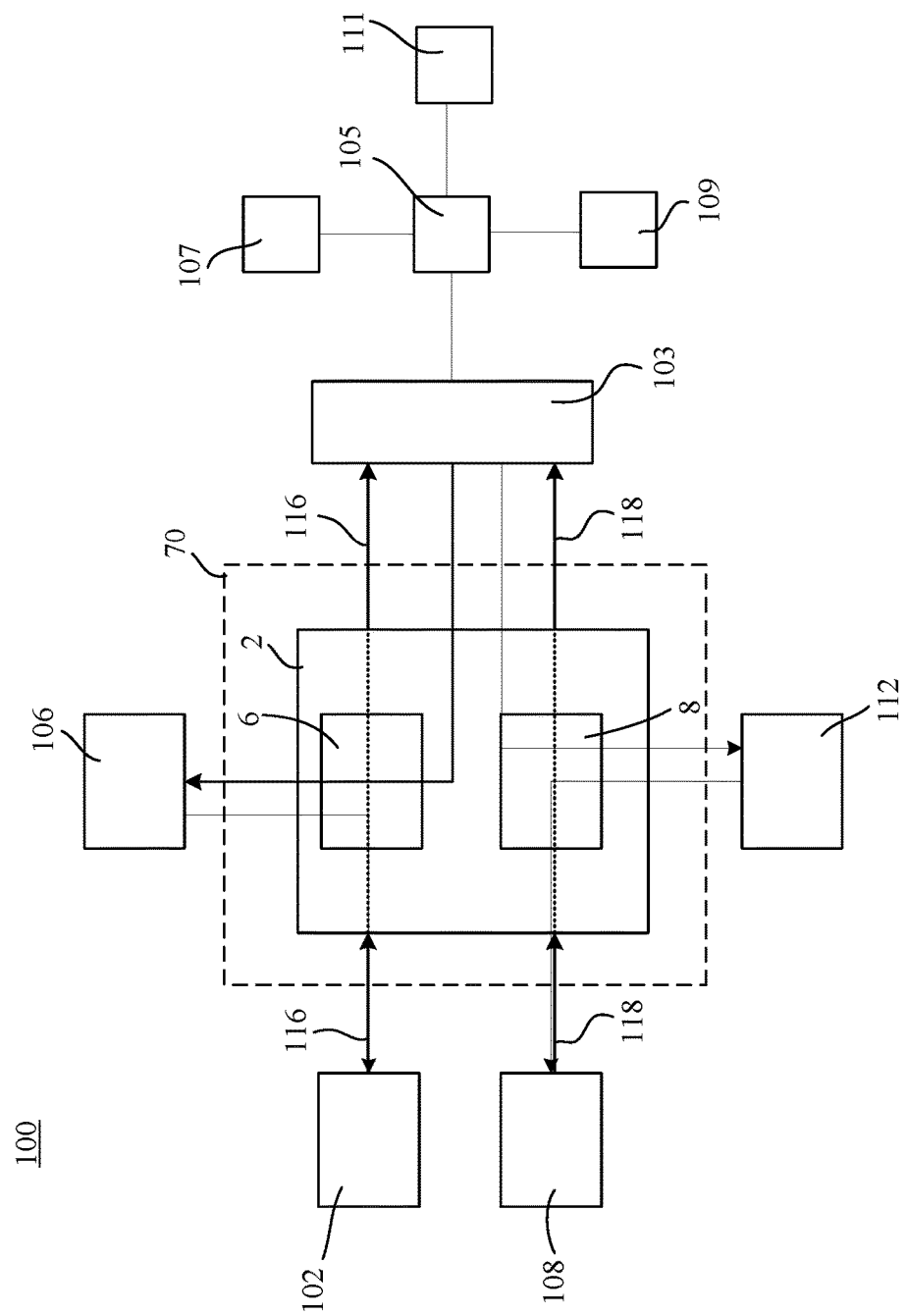
FIG. 18 shows an embodiment of the system.

In an embodiment, system 100, as shown in FIG. 13, is configured to determine, e.g., the sample condition. System 100 includes article 2 optionally disposed in container 70. Reference laser 102 (see, e.g., FIG. 18) produces reference light 116 and measurement light 118 that is communicated to reference optical cavity 10 and sample cavity 16 subsequently disposed into a light combiner 103. Further, the light from the combiner is disposed onto a detector 105. Further, the electrical from 105 is disposed onto a beat frequency detector 111.

The beat frequency (signal 124, FIG. 14) is produced in detector 105 when sample and reference light combine on the detector 105. Further, signal 124 is disposed onto a beat frequency detector 111 from which the sample condition can be determined.

Sample and reference light detector 105 can be, e.g., a photodiode, photomultiplier, avalanche photodiode and the like. The Fabry-Pérot cavity can be used to determine pressure by measuring refractive index n or, equivalently, measuring the refractivity n−1.

Figure 19:
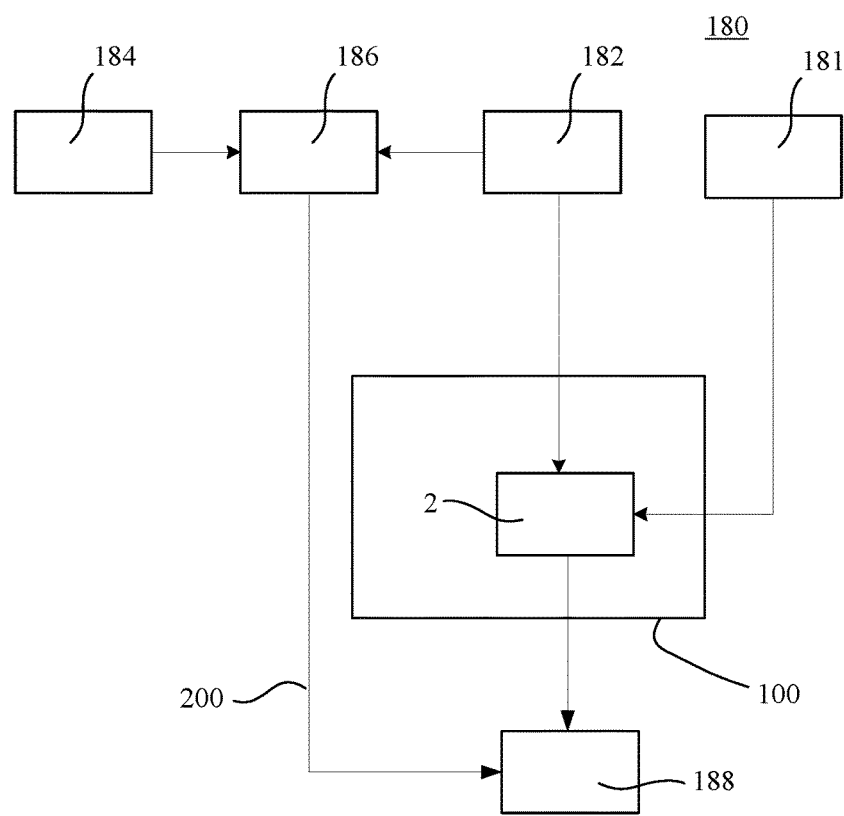
FIG. 19 shows an embodiment of a system.

According to an embodiment, as shown in FIG. 19, system 180 is configured to determine a pressure of an analyte gas. System 180 includes system 100 that includes article 2, which includes a substrate (e.g., substrate 4), reference optical cavity 6 disposed on substrate 4 and including reference cavity 10 interposed between a first pair of mirrors such that reference optical cavity 6 is configured to support a reference optical resonance and to receive a reference gas disposed in reference cavity 10, and sample optical cavity 8 disposed on substrate 4 and that includes sample cavity 16 interposed between a second pair of mirrors such that sample optical cavity 8 is configured to support a sample optical resonance and to receive a sample gas disposed in sample cavity 16. Article 2 can be disposed in container 70, and system 180 also can include optionally a reference gas source 181 in gas communication with reference optical cavity 6 to provide the reference gas. System 180 further includes sample gas source 182 in gas communication with sample optical cavity 8 to provide the sample gas and null detector 186 in gas communication with analyte gas source 184 and sample gas source 182. Null detector 186 is configured to produce a response (e.g., an electrical signal) to a difference in pressure between a pressure analyte gas and a pressure of sample gas in sample cavity 16. Additionally, system 180 includes analyzer 188 that is configured to receive the response from null detector 186 and to determine a pressure of the analyte gas, based on the response from the null detector and the beat frequency determined from the difference in frequency in sample light from sample optical cavity 8 and reference light from the reference optical cavity 6.

In an embodiment, analyte gas source 184 provides analyte gas to null detector 186. Additionally, sample gas source 182 provides samples gas to null detector 186 and sample optical cavity 8 of article 2. Null detector 186 is configured to detect a pressure difference between the pressure of the analyte gas and the pressure of the sample gas in sample optical cavity 16 and to produce null detector signal 200 that represents the pressure difference. To determine an absolute pressure of the analyte gas in analyte gas source 184, analyzer 188 receives reference light 116 and sample light 118 from article 2; produces reference signal 120, sample signal 122, and composite signal 124 (from signals 120, 122); receives a refractive index of the analyte gas (e.g., from a database or independent measure of the refractive index); receives the temperature of article 2 (e.g., from a secondary temperature sensor such as platinum resistance thermometer); determines the pressure of the sample gas in sample optical cavity 16 (from, e.g., the beat frequency in contained in the composite signal 124, temperature of the article, and the like); receives the null detector signal 200; determines the pressure difference from the null detector signal 200 (e.g., using a look-up table or analytical formula); and combines the pressure of the sample gas and the pressure difference to determine the absolute pressure of the analyte gas. In this manner, system 180 can be used as a barometric sensor to determine the absolute pressure of the analyte gas.

It is contemplated that analyte gas source 184, sample gas source 182, reference gas source (not shown), and secondary sample gas source (not shown) are independently a member in which the respective gas is disposed (e.g., a cylinder, tank, and the like), a gas line open to the atmosphere (e.g., earth's atmosphere), and the like.

In an embodiment, a process to detect an analyte gas in a composition includes providing article 2, adjusting a pressure of reference optical cavity 6 to be vacuum, adjusting a pressure of sample optical cavity 8 to be vacuum, introducing a reference light to reference optical cavity 6, adjusting the reference light to reference optical cavity 6 (e.g., locking the reference light to reference optical cavity 6), introducing a sample light to sample optical cavity 8, adjusting the sample light to sample optical cavity 8 (e.g., locking the reference light to sample optical cavity 8), transmitting the reference light from reference optical cavity 6, transmitting the sample light from sample optical cavity 8, receiving (by a detector) the sample light and reference light, and determining the beat frequency based on the difference in frequencies of the sample light and the reference light. The process also includes disposing the composition (wherein the composition includes a sample gas and an analyte gas) in sample optical cavity 8, adjusting a pressure of the composition in sample cavity 16, adjusting the sample light to sample optical cavity 8 in a presence of the composition, transmitting the sample light from sample optical cavity 8 to the detector, determining a beat frequency from the difference in the frequencies of the sample light and the reference light, determining an index of refraction of the composition based on a pressure and temperature of the composition in sample optical cavity 8 and the beat frequency. The process further includes optionally determining a chemical identity of component gases in the composition. Given the chemical identities of the component gases in the composition, the process includes determining a relative amount of the analyte gas in the composition based on the refractive index of the analyte gas, refractive index of the composition, and refractive index of every component in the sample gas to detect the analyte gas in the composition.

Determining the chemical identity of the component gases in the composition can be achieved by an analytical methodology such as gas chromatography, mass spectrometry, and the like. Such a methodology can qualitatively provide the chemical identities of the component gases in the composition. Further, the sample gas and the analyte gas independently can be subjected to the analytical methodology.

In a specific embodiment, the chemical identities of the component gases in the composition include carbon dioxide and air, wherein the analyte gas and sample gas respectively are carbon dioxide and air. Here, the analyte gas (carbon dioxide) in the composition is detected by determining the index of refraction of the composition using article 2 and determining a relative amount of the carbon dioxide in the composition based on the refractive index of the composition determined by article 2 and the refractive index of the analyte gas (carbon dioxide) and individual components in the sample gas (air) provided from an independent source.

It is contemplated that article 2 and processes herein have numerous advantageous benefits and properties. Article 2 provides robust, sensitive, and fast optical-based determination of pressure, temperature, or refractive index of a gas. Further, article 2 can be used advantageously as an internal reference standard. Moreover, article 2 can be used to determine density. Article 2 can be a monolithic structure or can include individual pieces that are interconnected.

Article 2 can be an arbitrary size and maintain its functionality. A longest linear dimension of article 2 can be selected based on a number density of sample gas, a wavelength of sample light used to produce a standing wave in sample cavity 16, and the like.

In some embodiments, the cavities include a length that is substantially fixed. In certain embodiments, the cavities include a length that is selectively variable and while selected parameters (e.g. Pressure, temperature) are held constant during determination of a sample condition. In an embodiment, the substrate has a coefficient of thermal expansion in an axial direction of the reference cavity or sample cavity that is fractionally less than or equal to $3 \times 10^{-8}/°$ C.

The articles and processes herein are illustrated further by the following Examples, which are non-limiting.

EXAMPLES

Example 1. Article with Exposed Sample Cavity

An article was fabricated in disposed in a container. The article was made from a block of ULE glass with holes and a slot drilled into it and polished. The ends were polished parallel and mirrors (coating on ULE substrate) were contacted to the ends.

Figure 20A:
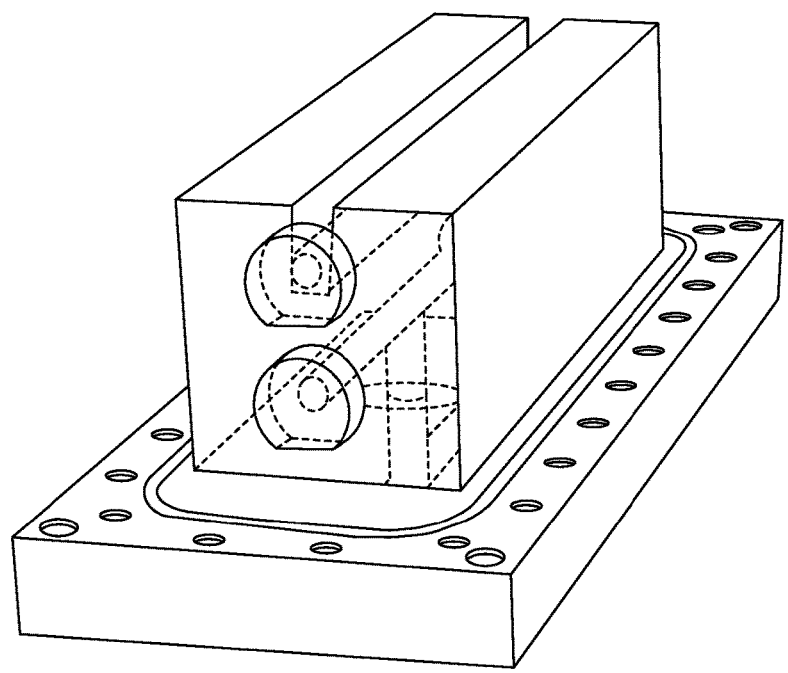
FIGS. 20A, 20B, 20C, and 20D show photographs of an article disposed in a container according to Example 1.
Figure 20B:
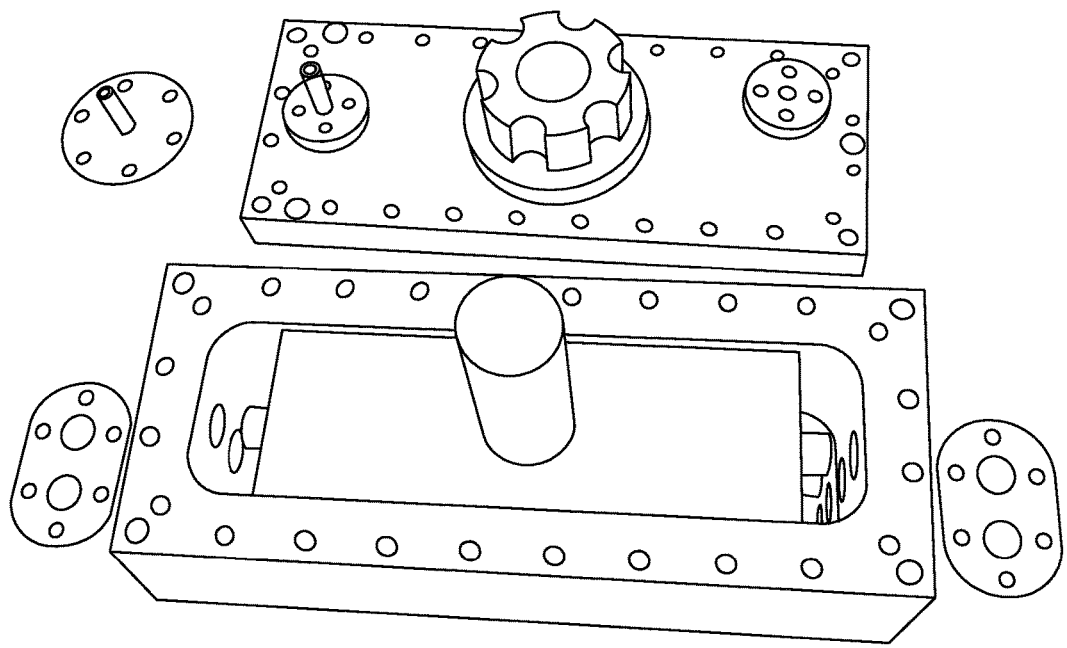
Figure 20C:
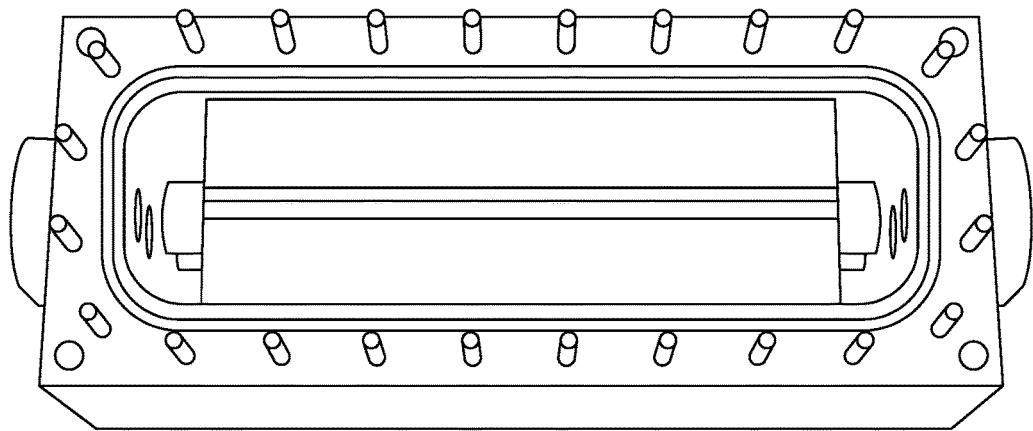
Figure 20D:
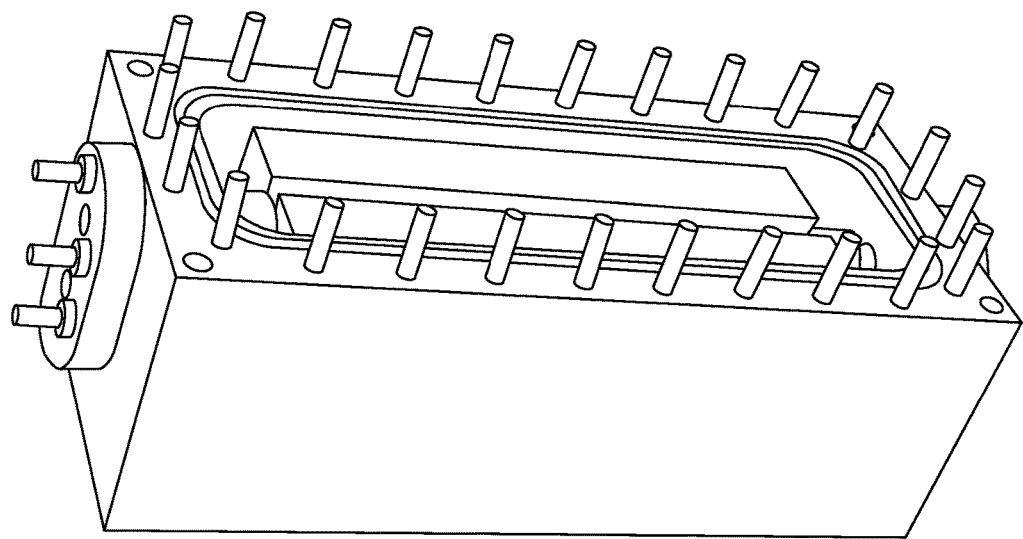

A photograph of an article disposed on a bottom lid of a container is shown in FIG. 20A. Here, the sample cavity is exposed and not fully contained in the substrate. FIG. 20B is a photograph that shows components of the container and disposition of the article (from a bottom view of the article) in a central portion of the container. FIG. 20C is a photograph that shows a top view of the article. FIG. 20D is a photograph that shows a side view of the article in the container. The fixed length optical cavity when disposed in the temperature controlled vacuum chamber was subjected to a pressure varied from $1 \times 10^{-7}$ torr to 760 torr.

Example 2. Article with Non-Exposed Sample Cavity

Figure 21:
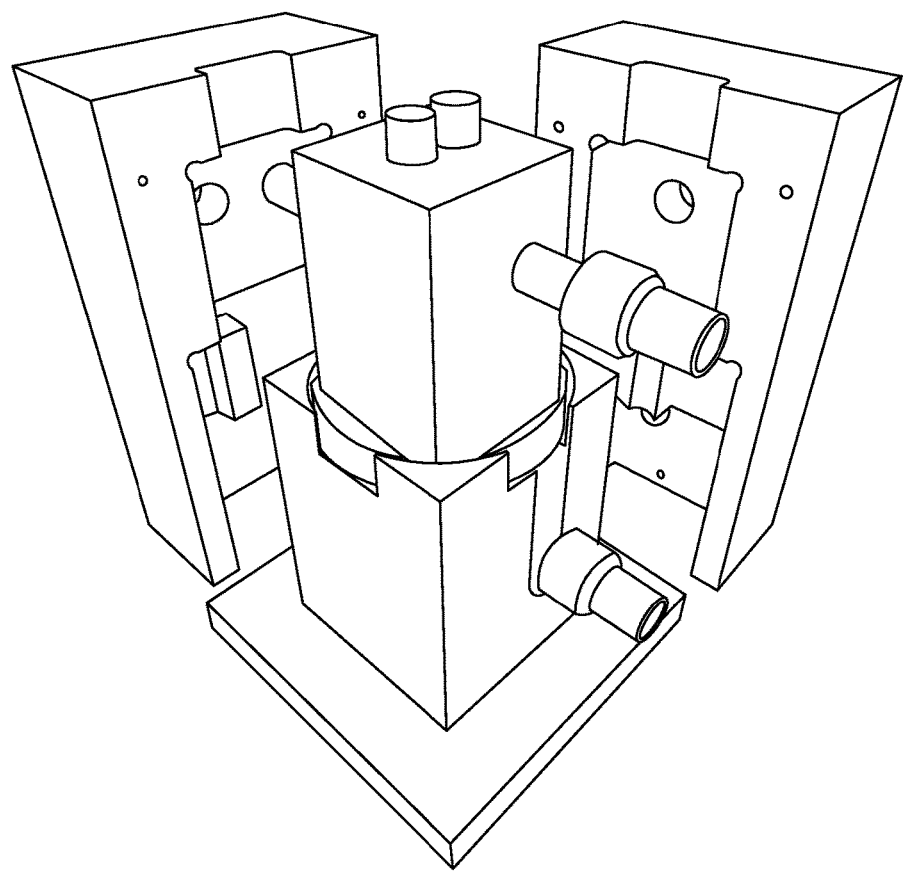
FIG. 21 shows a photograph of an article disposed in the container according to Example 2.

A photograph of an article disposed on a container is shown in FIG. 21. Here, the sample cavity is unexposed and fully contained in the substrate. A top lid of the container is shown on the left hand side of the photograph, and the bottom lid of the container is shown on the right-hand side of the photograph. The article includes a pair of reference couplers and reference gas paths and also a pair of sample couplers and sample gas paths. The cavity was made of the substrate material for high purity applications. The article was mounted at the center to reduce effect of vertical vibrations.

Example 3. Measurement of Cavity Linewidth

Figure 22:
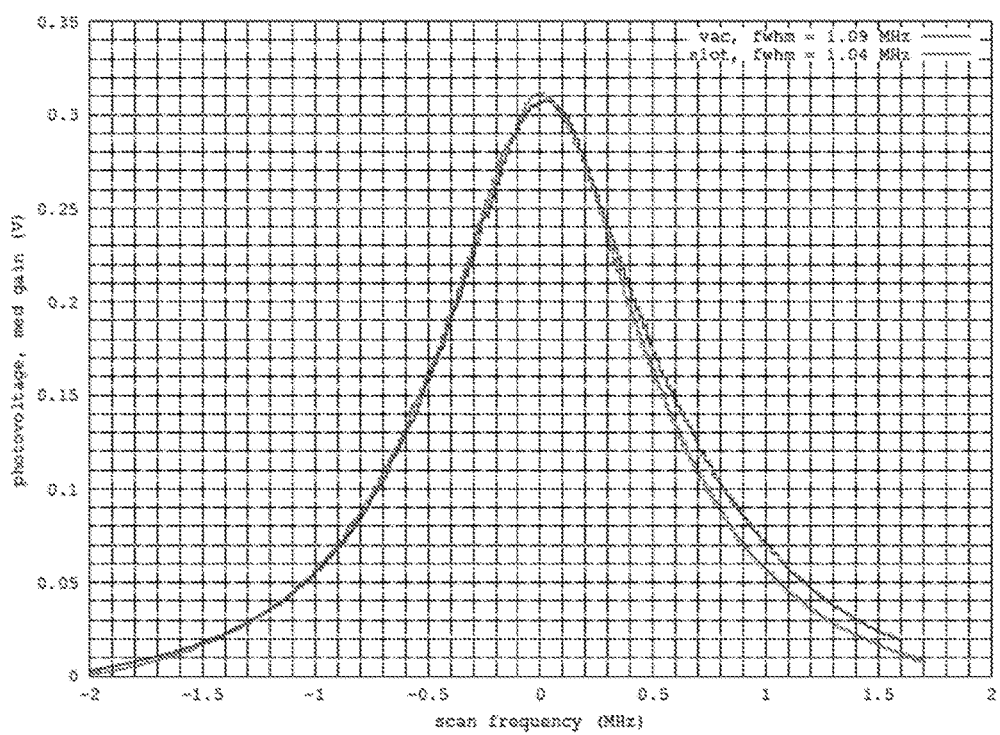
FIG. 22 shows a graph of voltage versus scan frequency according to Example 3.

The article described in Example 1 was used to acquire a graph of photovoltage versus scan frequency is shown in FIG. 22 shows that the finesse of the cavities are appropriate.

Example 4. Determination of Free Spectral Range Reference Cavity

Figure 23A:
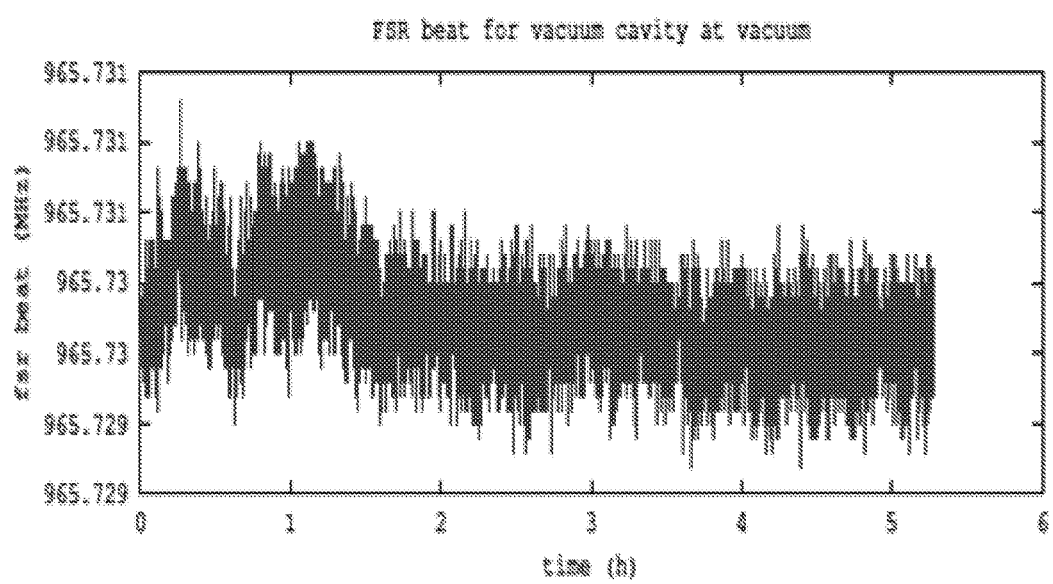
FIGS. 23A and 23B respectively show a graph of free spectral range beat versus time according to Example 4.
Figure 23B:
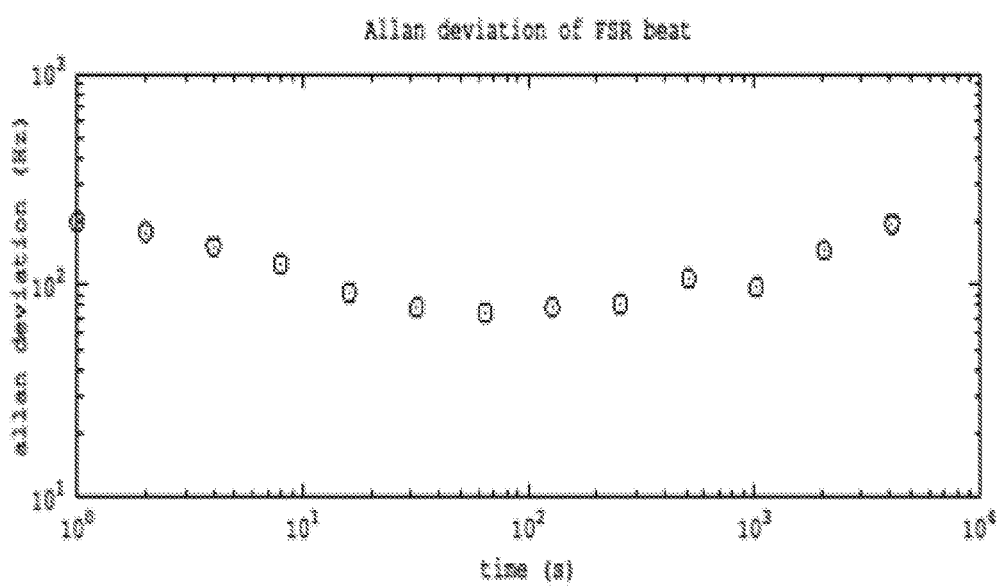

The article described in Example 1 was used to acquire free spectral range of the reference cavity. Here, two lasers were locked to adjacent cavity modes, and the beat between the two lasers was measured, in order to determine the free spectral range of the cavity. Beat frequency versus time is shown in FIG. 23A. Similarly, a graph of Allan deviation versus time is shown in FIG. 23B. These graphs show that the free spectral range can be determined with noise well below 1 part per million, enabling pressure measurements of comparable uncertainty.

Example 5. Determination of Free Spectral Range Sample Cavity

Figure 23C:
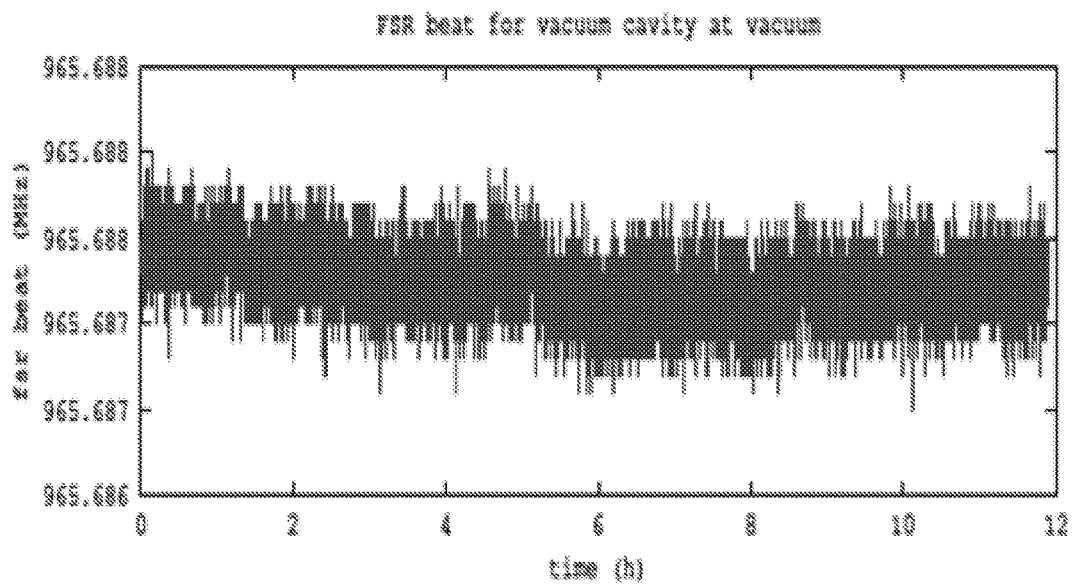
FIGS. 23C and 23D respectively show a graph of free spectral range beat versus time according to Example 4.
Figure 23D:
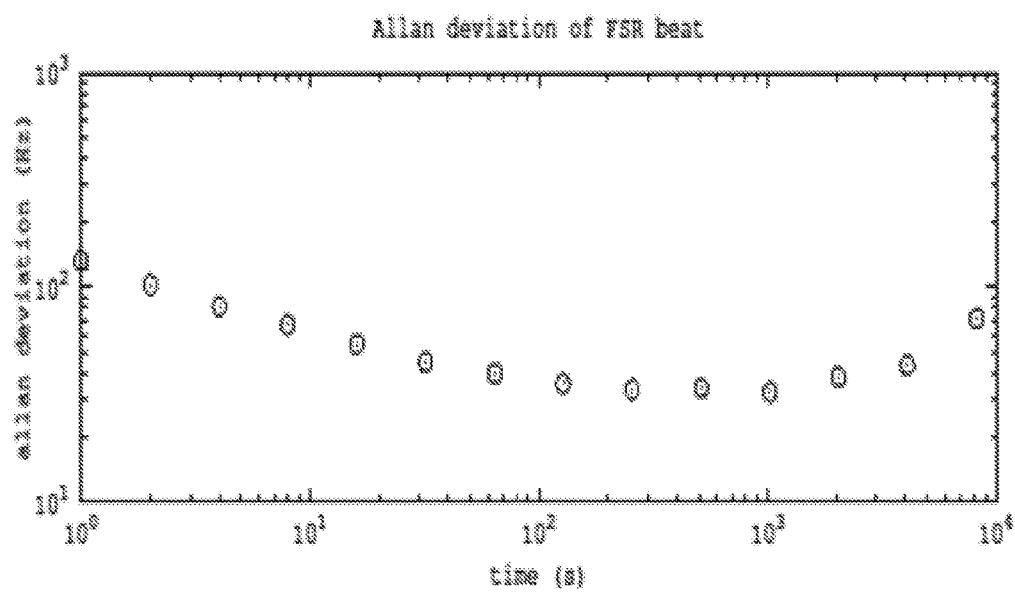

The article described in Example 1 was used to acquire free spectral range of the sample cavity. Here, two lasers were locked to adjacent cavity modes, and the beat between the two lasers was measured, in order to determine the free spectral range of the cavity. A graph of the beat versus time is shown in FIG. 23C. Similarly, a graph of Allan deviation versus time is shown in FIG. 23D. These graphs show that the free spectral range can be determined with noise well below 1 part per million, enabling pressure measurements of comparable uncertainty.

Example 6

Figure 24A:
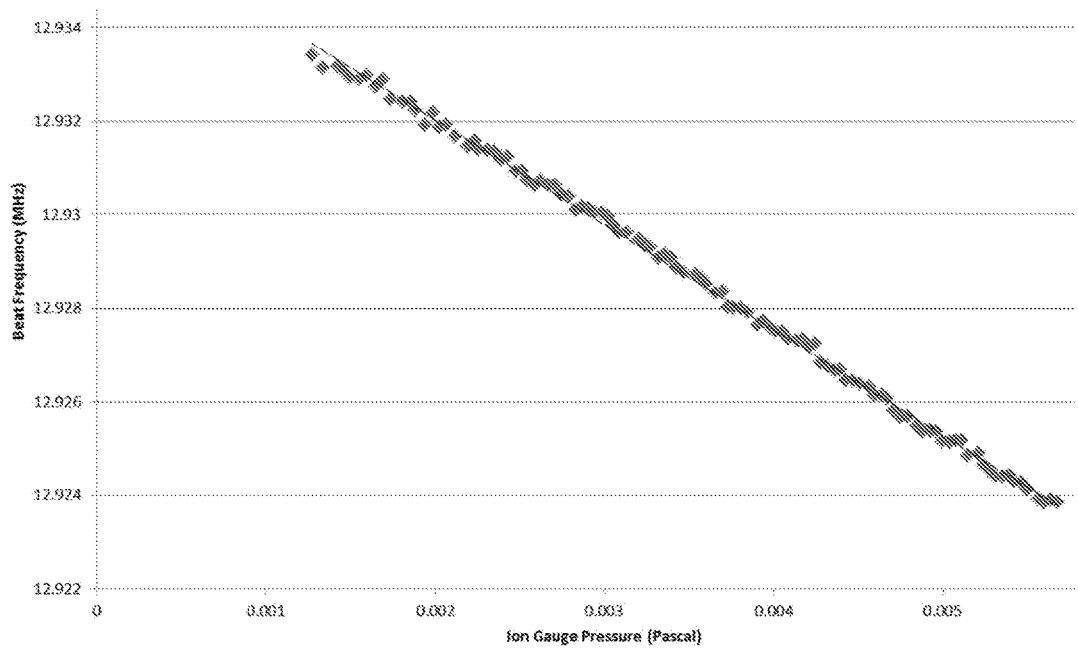
FIG. 24A shows a graph of beat frequency versus ion will pressure according to Example 5.
Figure 24B:
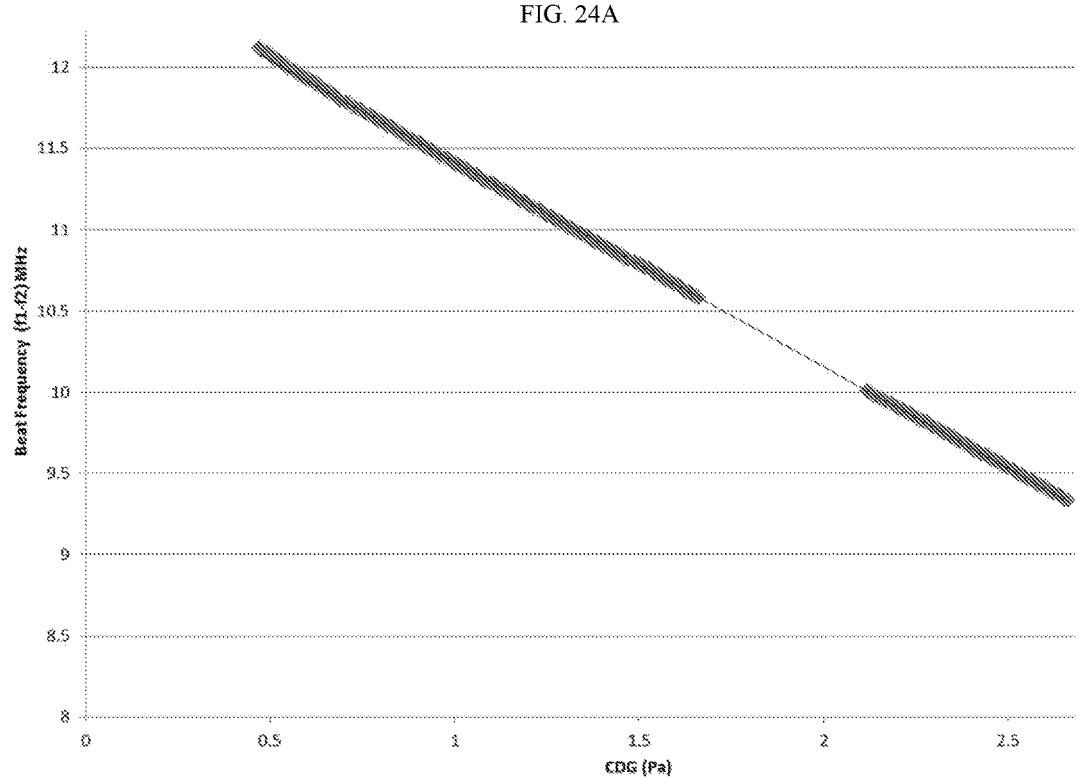
FIG. 24B shows a graph of beat frequency versus CDG pressure according to Example 6.

Sensitivity of article using ion gauge and a capacitance diaphragm gauge (CDG). FIGS. 24A and 24B are graphs of beat frequency versus ion gauge pressure (FIG. 24A) or CDG (FIG. 24B), which shows the response of the article.

Example 7

Figure 25A:
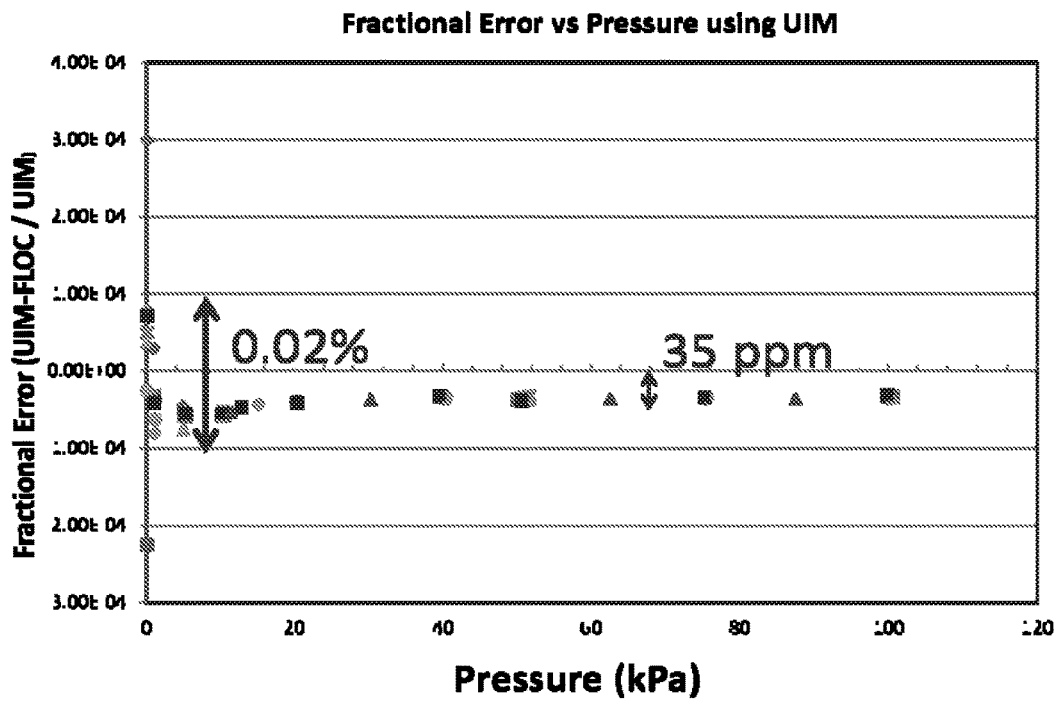
FIG. 25A shows a graph of fractional error versus pressure according to Example 7.
Figure 25B:
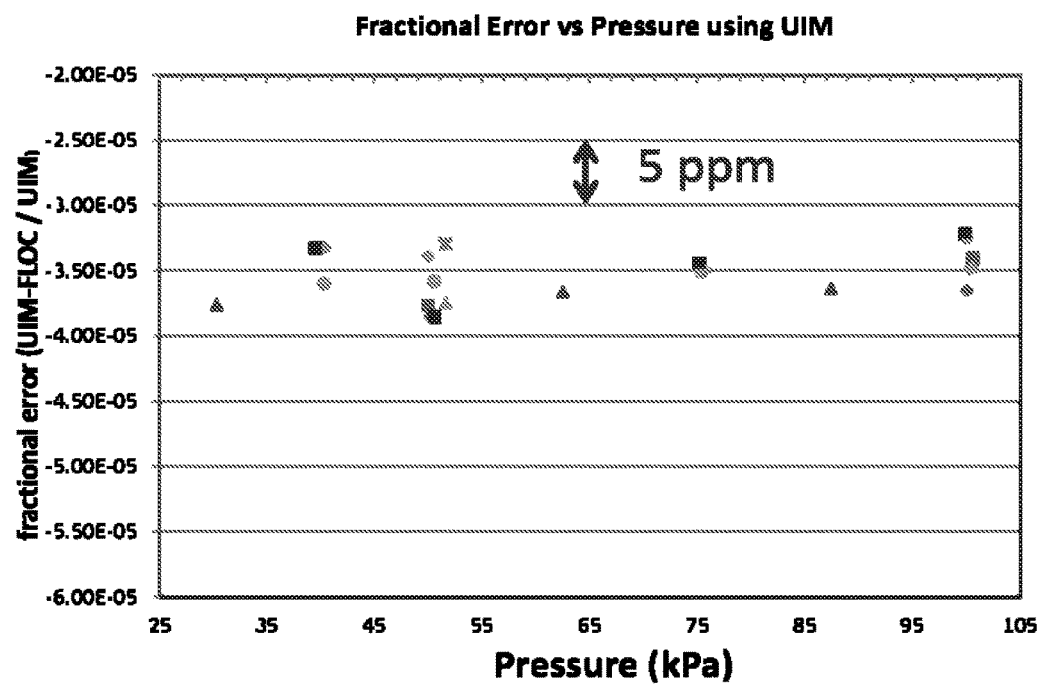
FIG. 25B shows a graph of fractional error versus pressure according to Example 8.

The article described in Example 1 was used to acquire a pressure of a gas, and the pressure of the gas also was measured with the NIST primary pressure standard, also referred to as the NIST Ultrasonic Interferometer Manometer (UIM). FIG. 25A shows the difference between the pressure as measured by the article describe in Example 1 and the NIST UIM 8 days of operation. At higher pressure, a 35 parts in $10^6$ difference is observed between the UIM measurement and that obtained by the article using a beat frequency determination, demonstrating surprising accuracy of the article. FIG. 25B shows the repeatability of the article described in example 1 is 5 parts in $10^6$ (or better) from 30 kPa to 100 kPa. This is comparable to the NIST UIM primary pressure standard, which is the US national standard for pressure measurement.

The article described in Example 1 was used to acquire a beat frequency signal proportional to pressure. Here, the working gas is nitrogen, and the beat frequency was measured as a function of nitrogen pressure as measured by a commercial ionization gauge. A graph of beat frequency versus ion gauge pressure is shown in FIG. 24A. Similarly, a graph of beat frequency versus pressure as measured by a CDG is shown in FIG. 24B. The results show the high precision of article 1 for pressure measurements, and demonstrate pressure limited resolution at 0.1 millipascal (7.5× $10^{-7}$ Torr) and linear pressure measurement response.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances. It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. An article comprising:
   a substrate;
   a reference optical cavity disposed on the substrate and comprising a reference cavity, the reference optical cavity being configured to support a reference optical resonance and to maintain an axial length of the reference cavity; and
   a sample optical cavity disposed on the substrate and comprising a sample cavity, the sample optical cavity being configured to support a sample optical resonance and to maintain an axial length of the sample cavity.

2. The article of claim 1, wherein the reference optical cavity further comprises:
   a first reference cavity mirror disposed at a first end of the reference cavity; and
   a second reference cavity mirror disposed at a second end of the reference cavity and opposing the first reference cavity mirror, wherein the reference optical cavity is configured to receive a reference gas disposed in the reference cavity and interposed between the first reference cavity mirror and the second reference cavity mirror.

3. The article of claim 2, wherein the sample optical cavity further comprises:
   a first sample cavity mirror disposed at a first end of the sample cavity; and
   a second sample cavity mirror disposed at a second end of the sample cavity and opposing the first sample cavity mirror, wherein the sample optical cavity is configured to receive a sample gas disposed in the sample cavity and interposed between the first sample cavity mirror and the second sample cavity mirror.

4. The article of claim 3, further comprising a reference gas path in gas communication with the reference cavity and configured to provide the reference gas to the reference optical cavity.

5. The article of claim 3, further comprising a sample gas path in gas communication with the sample cavity and configured to provide the sample gas to the sample optical cavity.

6. The article of claim 3, further comprising a secondary sample optical cavity disposed on the substrate.

7. The article of claim 6, wherein the secondary sample optical cavity comprises:
   a secondary sample cavity disposed on the substrate; and
   a primary mirror disposed at a first end of the secondary sample cavity; and
   a secondary mirror disposed at a second end of the secondary sample cavity and opposing the primary mirror, wherein the secondary sample optical cavity is configured to receive a secondary sample gas disposed in the secondary sample cavity and interposed between the primary mirror and the secondary mirror.

8. An article comprising:
   a first substrate;
   a second substrate spaced apart from the first substrate and opposingly disposed to the first substrate;
   a plurality of first mirrors disposed on the first substrate;
   a plurality of second mirrors disposed on the second substrate;
   a variable length member interposed between the first substrate and the second substrate and comprising an internal hollow portion;
   a reference optical cavity configured to support a reference optical resonance and comprising:
      a reference cavity; and
      a first pair of mirrors comprising:
         one of the first mirrors; and
         one of the second mirrors, such that the first pair of mirrors is opposingly arranged to one another, and the reference cavity is interposed between the first pair of mirrors and comprises the internal hollow portion; and
   a sample optical cavity configured to support a sample optical resonance and comprising:
      a sample cavity; and
      a second pair of mirrors, different from the first pair of mirrors, and comprising:
         one of the first mirrors; and
         one of the second mirrors, such that the second pair of mirrors is opposingly arranged to one another, and the sample cavity is interposed between the second pair of mirrors.

9. The article of claim 8, wherein a length of the sample cavity is selectively adjustable, and a length of the reference cavity is selectively adjustable.

10. The article of claim 9, wherein the reference optical cavity is configured to receive a reference gas disposed in the reference cavity and interposed between first pair of mirrors.

11. The article of claim 10, wherein the sample optical cavity is configured to receive a sample gas disposed in the sample cavity and interposed between the second pair of mirrors.

12. The article of claim 11, further comprising a reference gas path in gas communication with the reference cavity and configured to provide the reference gas to the reference optical cavity.

13. The article of claim 12, further comprising a sample gas path in gas communication with the sample cavity and configured to provide the sample gas to the sample optical cavity.

14. The article of claim 13, further comprising a secondary sample optical cavity comprising:
   a secondary sample cavity; and
   a third pair of mirrors comprising:
      one of the first mirrors; and
      one of the second mirrors, such that the third pair of mirrors is opposingly arranged to one another, and the secondary sample cavity is interposed between the third pair of mirrors, wherein the secondary sample optical cavity is configured to receive a secondary sample gas disposed in the secondary sample cavity and interposed between the third pair of mirrors.

15. A process for determining a sample condition, the process comprising:
    introducing a reference light to a reference cavity;
    adjusting the reference light to the reference cavity;
    transmitting the reference light from the reference cavity;
    introducing a sample light to a sample cavity;
    adjusting the sample light to the sample cavity;
    transmitting the sample light from the sample cavity;
    detecting the sample light;
    providing feedback for locking the reference light to the reference cavity;
    providing feedback for locking the sample light to the sample cavity;
    combining the reference light with the sample light;
    detecting a beat frequency, based on the reference light and the sample light; and
    determining a sample condition, based on the beat frequency.

16. The process of claim 15, wherein the sample condition comprises pressure, temperature, or refractive index.

17. A process for determining a sample condition, the process comprising:
    introducing a reference light to a reference cavity;
    adjusting the reference light to the reference cavity;
    transmitting the reference light from the reference cavity;
    introducing a sample light to a sample cavity;
    adjusting the sample light to the sample cavity;
    transmitting the sample light from the sample cavity;
    detecting the sample light;
    providing feedback for locking the reference light to the reference cavity;
    providing feedback for locking the sample light to the sample cavity;
    combining the reference light from the reference cavity with the sample light from the sample cavity;
    detecting a beat frequency, based on the reference light in the sample light; and
    determining a sample condition comprising a pressure of the sample gas, a temperature of the sample gas, or a refractive index of the sample gas.

18. The process of claim 17, wherein the secondary condition comprises a pressure, a temperature, or a refractive index.

* * * * *